(12) United States Patent
Ruchala et al.

(10) Patent No.: US 8,716,246 B2
(45) Date of Patent: May 6, 2014

(54) AZUVIRIN PEPTIDES

(75) Inventors: Piotr P. Ruchala, Los Angeles, CA (US); Robert I. Lehrer, Santa Monica, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/342,710

(22) Filed: Jan. 3, 2012

(65) Prior Publication Data

US 2013/0029903 A1 Jan. 31, 2013

Related U.S. Application Data

(60) Provisional application No. 61/429,414, filed on Jan. 3, 2011.

(51) Int. Cl.

| | |
|---|---|
| *A61K 38/10* | (2006.01) |
| *C07K 7/00* | (2006.01) |
| *A61P 35/00* | (2006.01) |
| *A61P 31/14* | (2006.01) |
| *A61K 51/08* | (2006.01) |

(52) U.S. Cl.
CPC . *A61K 38/10* (2013.01); *C07K 7/00* (2013.01); *A61K 51/08* (2013.01)
USPC ........... 514/21.5; 514/3.7; 514/19.3; 530/326

(58) Field of Classification Search
CPC ....... A61K 38/00; A61K 38/10; A61K 51/08; C07K 14/21; C07K 7/00
See application file for complete search history.

(56) References Cited

U.S. PATENT DOCUMENTS

| | | | |
|---|---|---|---|
| 7,608,618 | B2 | 10/2009 | Kesicki et al. |
| 2008/0221015 | A1 | 9/2008 | Chaudhari et al. |
| 2009/0286719 | A1 | 11/2009 | Das Gupta et al. |

OTHER PUBLICATIONS

Micewicz et al, Small Azurin Derived Peptide Targets Ephrin Receptors for Radiotherapy, Int J Pept Res Ther, 2011, 17, pp. 247-257.*
Definition of moiety, from http://dictionary.reference.com/browse/moiety, pp. 1-3, accessed Aug. 26, 2010.*
Brannan; et al. "Expression of the receptor tyrosine kinase EphA2 is increased in smokers and predicts poor survival in non-small cell lung cancer", Clin Cancer Res (Jul. 2009), 15(13):4423-4430.
Castaño; et al. "EPH receptors in cancer", Histol Histopathol (Aug. 2008), 23(8):1011-1023.
Chaudhari; et al. "Cupredoxin-cancer interrelationship: azurin binding with EphB2, interference in EphB2 tyrosine phosphorylation, and inhibition of cancer growth", Biochemistry (Feb. 2007), 46(7):1799-1810.
Yamada; et al. "Apoptosis or growth arrest: Modulation of tumor suppressor p53's specificity by bacterial redox protein azurin", PNAS (Apr. 2004), 101(14):4770-4775.

* cited by examiner

*Primary Examiner* — Julie Ha
*Assistant Examiner* — Li Ni Komatsu
(74) *Attorney, Agent, or Firm* — Bozicevic, Field & Francis LLP; Pamela J. Sherwood

(57) ABSTRACT

Azuvirin peptides are small peptide agents useful in delivering functional moieties, such as sensitizers, chemotherapeutic agents and the like to cancer cells expressing ephrin receptors. The peptides are also useful for administration to a patient suffering from a viral infection, or to an individual facing exposure to a viral infection, especially one caused by the Human Immunodeficiency Virus (HIV-1).

5 Claims, 12 Drawing Sheets

| Peptide | Sequence |
|---|---|
| AzV1 | GSGEKDSVTFDVSKLKEGEQYM-Phe-Phe-Cys-Thr-Phe-Pro-GHSA-Leu-Met-KGTLTLK (SEQ ID NO:1) |
| AzV2 | GSGEKDSVTFDVSKLKEGEQYM-Phe-Phe-Cys-Thr (SEQ ID NO:2) |
| AzV3 | EKDSVTFDVSKLKEGEQYM-Phe-Phe-Cys-Thr-Phe (SEQ ID NO:3) |
| AzV4 | VTFDVSKLKEGEQYM-Phe-Phe (SEQ ID NO:4) |
| AzV5 | VTFDVSKLKEpEQYM-Phe-Phe (SEQ ID NO:5) |
| AzV6 | FDVSKLKEGEQYM-Phe-Phe-Cys-Thr-Phe-Pro-GHSA-Leu-Met-K (SEQ ID NO:6) |
| AzV7 | FDVSKLKEGEQYM-Phe-Phe-Cys-Thr-Phe-Pro-GHSA-Leu-Cys-K (SEQ ID NO:7) |
| AzV8 | FDVSKLKEGEQYG-Gly-Gly-Cys-Thr-Phe-Pro-GHSA-Leu-Met-K (SEQ ID NO:8) |
| AzV9 | FDVSKLKEpEQYG-Gly-Gly-Cys-Thr-Phe-Pro-GHSA-Leu-Cys-K (SEQ ID NO:9) |
| AzV10 | FDVSKLKEGEQY (SEQ ID NO:10) |
| AzV11 | FDVSKLKEpEQY (SEQ ID NO:11) |
| AzV12 | Cys-Thr-Phe-Pro-GHSA-Leu-Met-K (SEQ ID NO:12) |
| AzV13 | Cys-Thr-Phe-Pro-GHSA-Leu-Cys-K (SEQ ID NO:13) |
| AzV14 | KLKEGEQYM-Phe-Phe-Cys-Thr-Phe-Pro-GH (SEQ ID NO:14) |
| AzV15 | KLKEpEQYM-Phe-Phe-Cys-Thr-Phe-Pro-GH (SEQ ID NO:15) |
| AzV16 | KLKEGEQYM-Phe-Phe-Cys-Thr-Phe-Pro-GHSA-Leu (SEQ ID NO:16) |
| AzV17 | KLKEGEQYM-Phe-Phe-Cys-Thr-Phe-Pro-GHSA-Leu-Met-K (SEQ ID NO:17) |
| AzV18 | KLKEGEQYM-Phe-Phe-Cys-Thr-Phe-Pro-GHSA-Leu-Met-KGTLTLK (SEQ ID NO:18) |
| AzV19 | EGEQYM-Phe-Phe-Cys-Thr-Phe-Pro-GH (SEQ ID NO:19) |
| AzV20 | EGEQYM-Phe-Phe-Cys-Thr-Phe-Pro-GHSA-Leu (SEQ ID NO:20) |
| AzV21 | EGEQYM-Phe-Phe-Cys-Thr-Phe-Pro-GHSA-Leu-Met-K (SEQ ID NO:21) |
| AzV22 | EGEQYM-Phe-Phe-Cys-Thr-Phe-Pro-GHSA-Leu-Met-KGTLTLK (SEQ ID NO:22) |
| AzV23 | YM-Phe-Phe-Cys-Thr-Phe-Pro-GH (SEQ ID NO:23) |
| AzV24 | YM-Phe-Phe-Cys-Thr-Phe-Pro-GHSA-Leu (SEQ ID NO:24) |
| AzV25 | YM-Phe-Phe-Cys-Thr-Phe-Pro-GHSA-Leu-Met-K (SEQ ID NO:25) |
| AzV26 | YM-Phe-Phe-Cys-Thr-Phe-Pro-GHSA-Leu-Met-KGTLTLK (SEQ ID NO:26) |
| AzV27 | YM-Phe-Phe-Ser-Thr-Phe-Pro-GHSA-Leu-Met-K (SEQ ID NO:27) |
| AzV28 | YM-Phe-Phe-Ctb-Thr-Phe-Pro-GHSA-Leu-Met-K (SEQ ID NO:28) |
| AzV29 | YM-Phe-Phe-Cts-Thr-Phe-Pro-GHSA-Leu-Met-K (SEQ ID NO:29) |
| AzV30 | YM-Phe-Phe-Cys-Thr-Phe-Pro-GHSA-Leu-Cys-K (SEQ ID NO:30) |
| AzV31 | YK-Cha-Cha-Cys-Tie-Cha-Oic-GHRT-Cha-Cys-K (SEQ ID NO:31) |
| AzV32 | YK-Cha-Cha-Cys-Tle-Cha-Oic-rHRT-Cha-Cys-k (SEQ ID NO:32) |
| AzV33 | YK-Cha-Cha-Cys--r--Cha-Oic-GHRT-Cha-Cys-k (SEQ ID NO:33) |
| AzV34 | Yk-Cha-Cha-Cys-Tie-Cha-Oic-GHRT-Cha-Cys-k (SEQ ID NO:34) |
| AzV35 | YK-Cha-Cha-Cys--r--Cha-Oic-rHRT-Cha-Cys-k (SEQ ID NO:35) |
| AzV36 | Yk-Cha-Cha-Cys-Tie-Cha-Oic-rHRT-Cha-Cys-k (SEQ ID NO:36) |
| AzV37 | Yk-Cha-Cha-Cys--r--Cha-Oic-GHRT-Cha-Cys-k (SEQ ID NO:37) |
| AzV38 | Yk-Cha-Cha-Cys--r--Cha-Oic-rHRT-Cha-Cys-k (SEQ ID NO:38) |
| AzV36-Nic | Yk$^{Nic}$-Cha-Cha-Cys-Tle-Cha-Oic-rHRT-Cha-Cys-k (SEQ ID NO:39) |
| AzV36-N icL | Yk$^{Nic}$-Cha-Cha-Cam-Tle-Cha-Oic-rHRT-Cha-Cam-k (SEQ ID NO:40) |
| AzV36-L | Yk-Cha-Cha-Cam-Tie-Cha-Oic-rHRT-Cha-Cam-k (SEQ ID NO:41) |
| AzV36-NicL-Clb | Clb-Yk$^{Nic}$-Cha-Cha-Cam-Tle-Cha-Oic-rHRT-Cha-Cam-k (SEQ ID NO:42) |
| AzV36-NicL-Mtx | Mtx-PEG$_3$-Yk$^{Nic}$-Cha-Cha-Cam-Tle-Cha-Oic-rHRT-Cha-Cam-k (SEQ ID NO:43) |

Figure 1

| | | |
|---|---|---|
| (human) Ephrin A1 | KFQ-Arg-Phe-Thr-Pro-Phr-Thr-Leu-GKEF-Lys-Glu-GHSY | (SEQ ID NO:47) |
| (human) Ephrin A2 | KFQ-Leu-Phe-Thr-Pro-Phe-Ser-Leu-GFEF-Arg-Pro-GHEY | (SEQ ID NO:48) |
| (human) Ephrin A3 | KFQ-Arg-Tyr-Ser-Ala-Phe-Ser-Leu-GYEF-His-Ala-GHEY | (SEQ ID NO:49) |
| (human) Ephrin A4 | KIQ-Arg-Phe-Thr-Pro-Phe-Ser-Leu-GFEF-Leu-Pro-GETY | (SEQ ID NO:50) |
| (human) Ephrin A5 | KFQ-Leu-Phe-Thr-Pro-Phe-Ser-Leu-GFEF-Arg-Pro-GREY | (SEQ ID NO:51) |
| (chicken) Ephrin A6 | KIQ-Arg-Phe-Thr-Pro-Phe-Ser-Leu-GFEF-Arg-Pro-GETY | (SEQ ID NO:52) |
| (human) Ephrin B1 | KFQ-Glu-Phe-Ser-Pro-Asn-Tyr-Met-GLEF-Lys-Lys-HHDY | (SEQ ID NO:53) |
| (human) Ephrin B2 | KFQ-Glu-Phe-Ser-Pro-Asn-Leu-Trp-GLEF-Gln-Lys-NKDY | (SEQ ID NO:54) |
| (human) Ephrin B3 | KFQ-Glu-Tyr-Ser-Pro-Asn-Leu-Trp-GHEF-Arg-Ser-HHDY | (SEQ ID NO:55) |
| (EphA2 ligand) SWL | SW-Leu-Ala-Tyr-Pro-Gly-Ala-Val-SYR | (SEQ ID NO:56) |
| (EphA2 ligand) YSA | Y-Ser-Ala-Tyr-Pro-Asp-Ser-Val-PMMS | (SEQ ID NO:57) |
| (EphB4 ligand) TNYL-RAW | TNY-Leu-Phe-Ser-Pro-Asn-Gly-Pro-IARA-Trp | (SEQ ID NO:58) |
| Azudn | EQY-Met-Phe-Phe-Cys-Thr-Phe-Pro-GHSA-Leu-Met-KGTL | (SEQ ID NO:59) |
| *AzV36-Mcl* | *Y-k*⁻ᴺᴴ²*-Cha-Cam-Ile-Cha-Oic-rNRT-Cha-Cam-k* | (SEQ ID NO:60) |
| APY | Ala-Pro-Tyr-Trp-Cys-Val-YRGS-Trp-Ser-C | (SEQ ID NO:61) |
| KYL | KYL-Pro-Tyr-Trp-Pro-Val-Leu-Ser-SL | (SEQ ID NO:62) |
| VTM | VTME-Ala-Ile-Asn-Leu-Ala-Phe-Pro-G | (SEQ ID NO:63) |
| NHW | NH-Trp-Leu-Asp-Thr-Leu-Phe-Pro-MHM | (SEQ ID NO:64) |

Figure 12

SEQUENCE LISTING

```
<160> NUMBER OF SEQ ID NOS: 64

<210> SEQ ID NO 1
<211> LENGTH: 41
<212> TYPE: PRT
<213> ORGANISM: Artificial Sequence
<220> FEATURE:
<223> OTHER INFORMATION: Synthetic peptide

<400> SEQUENCE: 1

Gly Ser Gly Glu Lys Asp Ser Val Thr Phe Asp Val Ser Lys Leu Lys
1               5                   10                  15

Glu Gly Glu Gln Tyr Met Phe Phe Cys Thr Phe Pro Gly His Ser Ala
            20                  25                  30

Leu Met Lys Gly Thr Leu Thr Leu Lys
        35                  40

<210> SEQ ID NO 2
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 2

Gly Ser Gly Glu Lys Asp Ser Val Thr Phe Asp Val Ser Lys Leu Lys
1               5                   10                  15

Glu Gly Glu Gln Tyr Met Phe Phe Cys Thr
            20                  25

<210> SEQ ID NO 3
<211> LENGTH: 24
<212> TYPE: PRT
<213> ORGANISM: Artificial Sequence
```

```
<220> FEATURE:
<223> OTHER INFORMATION: Synthetic peptide

<400> SEQUENCE: 3

Glu Lys Asp Ser Val Thr Phe Asp Val Ser Lys Leu Lys Glu Gly Glu
1               5                   10                  15

Gln Tyr Met Phe Phe Cys Thr Phe
            20

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Val Thr Phe Asp Val Ser Lys Leu Lys Glu Gly Glu Gln Tyr Met Phe
1               5                   10                  15

Phe

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Val Thr Phe Asp Val Ser Lys Leu Lys Glu Pro Glu Gln Tyr Met Phe
1               5                   10                  15

Phe

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

Phe Asp Val Ser Lys Leu Lys Glu Gly Glu Gln Tyr Met Phe Phe Cys
1               5                   10                  15

Thr Phe Pro Gly His Ser Ala Leu Met Lys
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic peptide

<400> SEQUENCE: 7

Phe Asp Val Ser Lys Leu Lys Glu Gly Glu Gln Tyr Met Phe Phe Cys
1               5                   10                  15

Thr Phe Pro Gly His Ser Ala Leu Cys Lys
            20                  25

<210> SEQ ID NO 8
<211> LENGTH: 26
<212> TYPE: PRT
<213> ORGANISM: Artificial sequence
<220> FEATURE:
<223> OTHER INFORMATION: Synthetic peptide
```

-continued

```
<400> SEQUENCE: 8

Phe Asp Val Ser Lys Leu Lys Glu Gly Glu Gln Tyr Gly Gly Gly Cys
1               5                   10                  15

Thr Phe Pro Gly His Ser Ala Leu Met Lys
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic peptide

<400> SEQUENCE: 9

Phe Asp Val Ser Lys Leu Lys Glu Pro Glu Gln Tyr Gly Gly Gly Cys
1               5                   10                  15

Thr Phe Pro Gly His Ser Ala Leu Cys Lys
            20                  25

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Phe Asp Val Ser Lys Leu Lys Glu Gly Glu Gln Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Phe Asp Val Ser Lys Leu Lys Glu Pro Glu Gln Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Cys Thr Phe Pro Gly His Ser Ala Leu Met Lys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Cys Thr Phe Pro Gly His Ser Ala Leu Cys Lys
1               5                   10

<210> SEQ ID NO 14
<211> LENGTH: 17
<212> TYPE: PRT
```

```
<213> ORGANISM: Artificial Sequence
<220> FEATURE:
<223> OTHER INFORMATION: Synthetic peptide

<400> SEQUENCE: 14

Lys Leu Lys Glu Gly Glu Gln Tyr Met Phe Phe Cys Thr Phe Pro Gly
1               5                   10                  15

His

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide

<400> SEQUENCE: 15

Lys Leu Lys Glu Pro Glu Gln Tyr Met Phe Phe Cys Thr Phe Pro Gly
1               5                   10                  15

His

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Lys Leu Lys Glu Gly Glu Gln Tyr Met Phe Phe Cys Thr Phe Pro Gly
1               5                   10                  15

His Ser Ala Leu
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic peptide

<400> SEQUENCE: 17

Lys Leu Lys Glu Gly Glu Gln Tyr Met Phe Phe Cys Thr Phe Pro Gly
1               5                   10                  15

His Ser Ala Leu Met Lys
            20

<210> SEQ ID NO 18
<211> LENGTH: 28
<212> TYPE: PRT
<213> ORGANISM: Artificial Sequence
<220> FEATURE:
<223> OTHER INFORMATION: Synthetic peptide

<400> SEQUENCE: 18

Lys Leu Lys Glu Gly Glu Gln Tyr Met Phe Phe Cys Thr Phe Pro Gly
1               5                   10                  15

His Ser Ala Leu Met Lys Gly Thr Leu Thr Leu Lys
            20                  25

<210> SEQ ID NO 19
<211> LENGTH: 14
<212> TYPE: PRT
<213> ORGANISM: Artificial Sequence
<220> FEATURE:
```

<223> OTHER INFORMATION: Synthetic peptide

<400> SEQUENCE: 19

Glu Gly Glu Gln Tyr Met Phe Phe Cys Thr Phe Pro Gly His
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide

<400> SEQUENCE: 20

Glu Gly Glu Gln Tyr Met Phe Phe Cys Thr Phe Pro Gly His Ser Ala
1               5                   10                  15

Leu

<210> SEQ ID NO 21
<211> LENGTH: 19
<212> TYPE: PRT
<213> ORGANISM: Artificial sequence
<220> FEATURE:
<223> OTHER INFORMATION: Synthetic peptide

<400> SEQUENCE: 21

Glu Gly Glu Gln Tyr Met Phe Phe Cys Thr Phe Pro Gly His Ser Ala
1               5                   10                  15

Leu Met Lys

<210> SEQ ID NO 22
<211> LENGTH: 25
<212> TYPE: PRT
<213> ORGANISM: Artificial Sequence
<220> FEATURE:
<223> OTHER INFORMATION: Synthetic peptide

<400> SEQUENCE: 22

Glu Gly Glu Gln Tyr Met Phe Phe Cys Thr Phe Pro Gly His Ser Ala
1               5                   10                  15

Leu Met Lys Gly Thr Leu Thr Leu Lys
            20                  25

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Tyr Met Phe Phe Cys Thr Phe Pro Gly His
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Tyr Met Phe Phe Cys Thr Phe Pro Gly His Ser Ala Leu
1               5                   10

```
<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

Tyr Met Phe Phe Cys Thr Phe Pro Gly His Ser Ala Leu Met Lys
1               5                   10                  15

<210> SEQ ID NO 26
<211> LENGTH: 21
<212> TYPE: PRT
<213> ORGANISM: Artificial Sequence
<220> FEATURE:
<223> OTHER INFORMATION: Synthetic peptide

<400> SEQUENCE: 26

Tyr Met Phe Phe Cys Thr Phe Pro Gly His Ser Ala Leu Met Lys Gly
1               5                   10                  15

Thr Leu Thr Leu Lys
            20

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

Tyr Met Phe Phe Ser Thr Phe Pro Gly His Ser Ala Leu Met Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa=Ctb-(L)-S-t-butyl-Cysteine

<400> SEQUENCE: 28

Tyr Met Phe Phe Xaa Thr Phe Pro Gly His Ser Ala Leu Met Lys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa= Cts-(L)-S-t-butylthio-Cysteine

<400> SEQUENCE: 29

Tyr Met Phe Phe Xaa Thr Phe Pro Gly His Ser Ala Leu Met Lys
1               5                   10                  15

<210> SEQ ID NO 30
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 30

Tyr Met Phe Phe Cys Th

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa= Cha-(L)-cyclohexyl-Alanine
<220> FEATURE:
<221> NAME/KEY: MISC_FEATURE
<222> LOCATION: (4)..(4)
<223> OTHER INFORMATION: Xaa= Cha-(L)-cyclohexyl-Alanine
<220> FEATURE:
<221> NAME/KEY: MISC_FEATURE
<222> LOCATION: (7)..(7)
<223> OTHER INFORMATION: Xaa= Cha-(L)-cyclohexyl-Alanine
<220> FEATURE:
<221> NAME/KEY: MISC_FEATURE
<222> LOCATION: (8)..(8)
<223> OTHER INFORMATION: Oic-(L)-Octahydroindole-2-carboxylic acid
<220> FEATURE:
<221> NAME/KEY: MISC_FEATURE
<222> LOCATION: (13)..(13)
<223> OTHER INFORMATION: Xaa= Cha-(L)-cyclohexyl-Alanine

<400> SEQUENCE: 33

Tyr Lys Xaa Xaa Cys Arg Xaa Xaa Gly His Arg Thr Xaa Cys Lys
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa=Cha-(L)-cyclohexyl-Alanine
<220> FEATURE:
<221> NAME/KEY: MISC_FEATURE
<222> LOCATION: (4)..(4)
<223> OTHER INFORMATION: Xaa= Cha-(L)-cyclohexyl-Alanine
<220> FEATURE:
<221> NAME/KEY: MISC_FEATURE
<222> LOCATION: (6)..(6)
<223> OTHER INFORMATION: Xaa= Tle-(L) tert-Leucine
<220> FEATURE:
<221> NAME/KEY: MISC_FEATURE
<222> LOCATION: (7)..(7)
<223> OTHER INFORMATION: Xaa= Cha-(L)-cyclohexyl-Alanine
<220> FEATURE:
<221> NAME/KEY: MISC_FEATURE
<222> LOCATION: (8)..(8)
<223> OTHER INFORMATION: Xaa= Oic-(L)-Octahydroindole-2-carboxylic acid
<220> FEATURE:
<221> NAME/KEY: MISC_FEATURE
<222> LOCATION: (13)..(13)
<223> OTHER INFORMATION: Xaa= Cha-(L)-cyclohexyl-Alanine

<400> SEQUENCE: 34

Tyr Lys Xaa Xaa Cys Xaa Xaa Xaa Gly His Arg Thr Xaa Cys Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<222> LOCATION: (3)..(3)
<223> OTHER INFORMATION: Xaa=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (7)..(7)
<223> OTHER INFORMATION: Xaa=Cha-(L)-cyclohexyl-Alanine
<220> FEATURE:
<221> NAME/KEY: MISC_FEATURE
<222> LOCATION: (8)..(8)
<223> OTHER INFORMATION: Xaa=Cha-(L)-cyclohexyl-Alanine
<220> FEATURE:
<221> NAME/KEY: MISC_FEATURE
<222> LOCATION: (13)..(13)
<223> OTHER INFORMATION: Xaa=Cha-(L)-cyclohexyl-Alanine

<400> SEQUENCE: 35

Tyr Lys Xaa Xaa Cys Arg Xaa Xaa Arg His Arg Thr Xaa Cys Lys
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa=Cha-(L)-cyclohexyl-Alanine
<220> FEATURE:
<221> NAME/KEY: MISC_FEATURE
<222> LOCATION: (4)..(4)
<223> OTHER INFORMATION: Xaa=Cha-(L)-cyclohexyl-Alanine
<220> FEATURE:
<221> NAME/KEY: MISC_FEATURE
<222> LOCATION: (6)..(6)
<223> OTHER INFORMATION: Xaa=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: Xaa=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine

<400> SEQUENCE: 36

Tyr Lys Xaa Xaa Cys Xaa Xaa Xaa Arg His Arg Thr Xaa Cys Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (7)..(7)
```

```
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine

<400> SEQUENCE: 37

Tyr Lys Xaa Xaa Cys Arg Xaa Xaa Gly His Arg Thr Xaa Cys Lys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine

<400> SEQUENCE: 38

Tyr Lys Xaa Xaa Cys Arg Xaa Xaa Arg His Arg Thr Xaa Cys Lys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
```

```
<400> SEQUENCE: 39

Tyr Lys Xaa Xaa Cys Xaa Xaa Xaa Arg His Arg Thr Xaa Cys Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
<220> FEATURE:
<221> NAME/KEY: MISC_FEATURE
<222> LOCATION: (14)..(14)
<223> OTHER INFORMATION: X=Cam-(L)-Sacetamidomethyl-Cysteine

<400> SEQUENCE: 40

Tyr Lys Xaa Xaa Xaa Xaa Xaa Xaa Arg His Arg Thr Xaa Xaa Lys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
```

```
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
<220> FEATURE:
<221> NAME/KEY: MISC_FEATURE
<222> LOCATION: (14)..(14)
<223> OTHER INFORMATION: X=Cam-(L)-Sacetamidomethyl-Cysteine

<400> SEQUENCE: 41

Tyr Lys Xaa Xaa Xaa Xaa Xaa Xaa Arg His Arg Thr Xaa Xaa Lys
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
<220> FEATURE:
<221> NAME/KEY: MISC_FEATURE
<222> LOCATION: (14)..(14)
<223> OTHER INFORMATION: X=Cam-(L)-Sacetamidomethyl-Cysteine

<400> SEQUENCE: 42

Tyr Lys Xaa Xaa Xaa Xaa Xaa Xaa Arg His Arg Thr Xaa Xaa Lys
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
```

```
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
<220> FEATURE:
<221> NAME/KEY: MISC_FEATURE
<222> LOCATION: (14)..(14)
<223> OTHER INFORMATION: X=Cam-(L)-Sacetamidomethyl-Cysteine

<400> SEQUENCE: 43

Tyr Lys Xaa Xaa Xaa Xaa Xaa Xaa Arg His Arg Thr Xaa Xaa Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine

<400> SEQUENCE: 44

Tyr Lys Xaa Xaa Cys Xaa Xaa Xaa Arg His Arg Thr Xaa Cys Lys
1               5                   10                  15

<210> SEQ ID NO 45
<211> LENGTH: 15
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine

<400> SEQUENCE: 45

Tyr Lys Xaa Xaa Cys Xaa Xaa Xaa Arg His Arg Thr Xaa Cys Lys
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: MISC_FEATURE
<222> LOCATION: (7)..(7)
<223> OTHER INFORMATION: X=Cha-(L)-cyclohexyl-Alanine
<220> FEATURE:
<221> NAME/KEY: MISC_FEATURE
<222> LOCATION: (8)..(8)
<223> OTHER INFORMATION: X=Oic-(L)-Octahydroindole-2-carboxylic acid
<220> FEATURE:
<221> NAME/KEY: MISC_FEATURE
<222> LOCATION: (13)..(13)
<223> OTHER INFORMATION: X=Cha-(L)-cyclohexyl-Alanine
<220> FEATURE:
```

```
<221> NAME/KEY: MISC_FEATURE
<222> LOCATION: (14)..(14)
<223> OTHER INFORMATION: X=Cam-(L)-Sacetamidomethyl-Cysteine

<400> SEQUENCE: 46

Tyr Lys Xaa Xaa Xaa Xaa Xaa Xaa Arg His Arg Thr Xaa Xaa Lys
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 47

Lys Phe Gln Arg Phe Thr Pro Phe Thr Leu Gly Lys Glu Phe Leu Glu
1               5                   10                  15

Gly His Ser Tyr
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Lys Phe Gln Leu Phe Thr Pro Phe Ser Leu Gly Phe Glu Phe Arg Pro
1               5                   10                  15

Gly His Glu Tyr
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Lys Phe Gln Arg Tyr Ser Ala Phe Ser Leu Gly Tyr Glu Phe His Ala
1               5                   10                  15

Gly His Glu Tyr
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Lys Ile Gln Arg Phe Thr Pro Phe Ser Leu Gly Phe Glu Phe Leu Pro
1               5                   10                  15

Gly Glu Thr Tyr
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 51

Lys Phe Gln Leu Phe Thr Pro Phe Ser Leu Gly Phe Glu Phe Arg Pro
1               5                   10                  15

Gly Arg Glu Tyr
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Lys Ile Gln Arg Phe Thr Pro Phe Ser Leu Gly Phe Glu Phe Arg Pro
1               5                   10                  15

Gly Glu Thr Tyr
            20

<210> SEQ ID NO 53
<211> LENGTH: 21
<212> TYPE: PRT
<213> ORGANISM: Artificial Sequence
<220> FEATURE:
<223> OTHER INFORMATION: Synthetic peptide

<400> SEQUENCE: 53

Lys Phe Gln Glu Phe Ser Pro Asn Thr Met Gly Leu Trp Glu Phe Lys
1               5                   10                  15

Lys His His Asp Tyr
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Lys Phe Gln Glu Phe Ser Pro Asn Leu Trp Gly Leu Glu Phe Gln Lys
1               5                   10                  15

Asn Lys Asp Tyr
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Lys Phe Gln Glu Thr Ser Pro Asn Leu Trp Gly His Glu Phe Arg Ser
1               5                   10                  15

His His Asp Tyr
            20

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

Ser Trp Leu Ala Tyr Pro Gly Ala Val Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide

<400> SEQUENCE: 57

Tyr Ser Ala Tyr Pro Asp Ser Val Pro Met Met Ser
1               5                   10

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide

<400> SEQUENCE: 58

Thr Asn Tyr Leu Phe Ser Pro Asn Gly Pro Ile Ala Arg Ala Thr
1               5                   10                  15

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Glu Gln Tyr Met Phe Phe Cys Thr Phe Pro Gly His Ser Ala Leu Met
1               5                   10                  15

Lys Gly Thr Leu
            20

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: conjugation with nicotinic acid via an amine
      bond
<220> FEATURE:
<221> NAME/KEY: MISC_FEATURE
<222> LOCATION: (3)..(3)
<223> OTHER INFORMATION: X=Cha-(L)-cyclohexyl-Alanine
<220> FEATURE:
<221> NAME/KEY: MISC_FEATURE
<222> LOCATION: (4)..(4)
<223> OTHER INFORMATION: X=Cha-(L)-cyclohexyl-Alanine
<220> FEATURE:
<221> NAME/KEY: MISC_FEATURE
<222> LOCATION: (5)..(5)
<223> OTHER INFORMATION: X=Cam-(L)-Sacetamidomethyl-Cysteine
<220> FEATURE:
<221> NAME/KEY: MISC_FEATURE
<222> LOCATION: (6)..(6)
<223> OTHER INFORMATION: X=Tle-(L) tert-Leucine
<220> FEATURE:
<221> NAME/KEY: misc_feature
<222> LOCATION: (7)..(7)
<223> OTHER INFORMATION: Xaa can be any naturally occurring amino acid

```
<220> FEATURE:
<221> NAME/KEY: MISC_FEATURE
<222> LOCATION: (8)..(8)
<223> OTHER INFORMATION: X=Cha-(L)-cyclohexyl-Alanine
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: X=Cha-(L)-cyclohexyl-Alanine

<400> SEQUENCE: 60

Tyr Lys Xaa Xaa Xaa Xaa Xaa Xaa Arg His Arg Thr Xaa Xaa Lys
1               5                   10                  15

<210> SEQ ID NO 61
<211> LENGTH: 12
<212> TYPE: PRT
<213> ORGANISM: Artificial Sequence
<220> FEATURE:
<223> OTHER INFORMATION: Synthetic peptide

<400> SEQUENCE: 61

Ala Pro Tyr Cys Val Tyr Arg Gly Ser Trp Ser Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide

<400> SEQUENCE: 62

Lys Tyr Leu Pro Tyr Trp Pro Val Leu Ser Ser Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic peptide

<400> SEQUENCE: 63

Val Thr Met Glu Ala Ile Asn Leu Ala Phe Pro Gly
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic peptide

<400> SEQUENCE: 64

Asn His Trp Leu Asp Thr Leu Phe Pro Met His Met
1               5                   10
```

AZUVIRIN PEPTIDES

BACKGROUND OF THE INVENTION

Targeted radiation therapy has been a mainstay of treatment for human cancers for decades. The development of compounds that sensitize malignancies to radiation has significantly enhanced its efficacy. The ability of "radio-sensitizer" compounds to improve therapy is dependent on their entry into cancerous cells. However, the toxic effects of most radio-sensitizing compounds on the body limit their administration to patients. Therefore, there is a great need to develop novel compounds or delivery systems that boost the uptake of radio-sensitizing compounds into tumors. Improved uptake of radio-sensitizing compounds into tumors could drastically improve the response to therapy and reduce the duration of treatment.

Ephrin receptors constitute the largest family of receptor tyrosine kinases. The family consists of 16 individual receptors (14 found in mammals), which are activated by nine ephrins (8 in mammals). Eph receptors and their ephrin ligands are both anchored onto the plasma membrane and are subdivided into two subclasses, A and B. Usually, EphA receptors (EphA1-A10) interact with glycosylphosphatidylinositol (GPI)-anchored ephrin-A ligands (ephrin-A1-A6), whereas EphB receptors (EphB1-B6) interact with transmembrane ephrin-B ligands (ephrin-B1-B3) that have a short cytoplasmic portion carrying both Src homology domain 2 and PDZ domain-binding motifs. A few examples of inter-class binding have also been reported. The extensive signaling network of Ephs and their ligands plays important roles in a great variety of processes, such as regulation of cell assembly, proliferation, migration, cell attachment and shape, axon guidance and synaptic plasticity, particularly during development. Recently they were also implicated in many physiological processes, including the regulation of insulin secretion, bone homeostasis, immune function, blood clotting, etc. It is noteworthy that ephrin B2 was found to specifically bind the attachment (G) glycoproteins of Nipah virus and Hendra virus to serve as a functional receptor for the entry of both viruses in animals and humans.

It is not surprising that Ephs play important roles in tumorigenesis and metastasis. The high levels of Ephs found in cancers may generate proliferative and survival signals, and influence angiogenesis in many tumor types, including lung, breast and prostate cancers. Consequently, an ability to modulate or target this family of receptors could possess therapeutic value. Modulation can be achieved with antibodies, soluble forms of Eph receptors and ephrin extracellular domains or low molecular weight antagonists. Such modulation, largely directed at the canonical ligand-receptor signaling pathways, is complicated by bi-directional signaling that can suppress as well as stimulate cancer growth.

Fewer attempts have been made to use overexpressed Eph receptors as molecular targets for the selective delivery of anti-cancer therapeutics. Among new anticancer therapeutics, small peptides have shown considerable promise based on their potent bioactivity and superb target specificity. Although peptide-based compounds with high affinity binding to selected ephrin receptors have been reported, their anticancer potential has not been evaluated.

Azurin (Azu), a small protein produced by the bacterial pathogen *Pseudomonas aeruginosa* possesses significant anticancer and antiviral activity. The protein binds to selected ephrin receptors, EphB2, EphA6, and to a lesser extent to EphA4 and EphA7, primarily through a short fragment of the protein, $Azu_{96-113}$. Development of therapeutic analogs of this protein are of interest.

Publications

Castaño et al. EPH receptors in cancer, Histol. Histopathol. 2008; 23(8): 1011-23; Brannan et al. Expression of the receptor tyrosine kinase EphA2 is increased in smokers and predicts poor survival in non-small cell lung cancer, Cancer Res. 2009; 15(13):4423-30; Chaudhari et al. Cupredoxin-cancer interrelationship: azurin binding with EphB2, interference in EphB2 tyrosine phosphorylation, and inhibition of cancer growth, Biochemistry 2007; 46(7): 1799-810.

SUMMARY OF THE INVENTION

Methods and compositions, including pharmaceutical formulations, are provided for the use of azuvirin peptides (AzV), which are synthetic short peptide analogs of azurin protein.

In some embodiments, azuvirin peptides are of interest for molecular targeting of tumor cells through binding to ephrin receptors expressed by tumor cells, including without limitation ephrin receptors EphA2, EphB2, and EphB4. Molecular targeting allows delivery of chemotherapeutic agents, including radiosensitizers, photodynamic sensitizer, and chemotherapy sensitizers, collectively referred to as sensitizers. Radiosensitizers of interest include, without limitation, nicotinamide, misonidazole, metronidazole, and the like. In some such embodiments, an effective dose of an azuvirin conjugated to a sensitizer is administered to an individual in a dose effective to sensitive a tumor, e.g. a solid tumor such as a carcinoma, to radiation or chemotherapy, where the effect of the radiation or chemotherapy is greater than the effect in the absence of the azuvirin conjugate. In some embodiments a pharmaceutical formulation comprising an effective dose of an azuvirin or an azuvirin conjugate with a pharmaceutically effective excipient is provided, e.g. in a unit dose.

In other embodiments, azuvirins are of interest for antiviral activity, where an azuvirin is brought into contact with a virus or cell in a dose effective to decrease infection of the cell by the virus. Some Azuvirins bind directly to the glycoproteins of important viral pathogens, including HIV-1 and herpes simplex viruses, or to host cell receptors that participate in viral entry, including DC-SIGN and ephrin receptor 82 (EphB2). Some AzVs possess potent antiviral activity toward HIV-1 and HSV-2. In some embodiments a pharmaceutical formulation is provided comprising an effective dose of an azuvirin or an azuvirin conjugate with a pharmaceutically acceptable excipient is provided.

BRIEF DESCRIPTION OF THE DRAWINGS

FIG. 1. List of synthesized AzV analogs. All peptides were synthesized as C-terminal amides. D-amino acids are showed as appropriate lowercase letters in bold style. Pairs of cysteins forming disulfide bridges are shaded. Abbreviations: Cha-(L)-cyclohexyl-Alanine, Ctb-(L)-S-t-butyl-Cysteine, Cts-p-S-t-butylthio-Cysteine, Cam-(L)-Sacetamidomethyl-Cysteine, Nic-Nicotinic acid, Oic-(L)-Octahydroindole-2-carboxylic acid, Tle-(L) tert-Leucine, r-(D)-Arginine, k-(D)-Lysine, PEG3-11-Amino-3,6,9-trioxaundecanoic acid, Clb-chlorambucil, Mtx-methotrexate.

FIG. 12. Comparison of corresponding sequences of ephrins (natural ligands of Ephs), peptides binding to ephrin receptors (TNYL-RAW binds to EphB4 [34], SWL and YSA bind EphA2 [33], APY, KYL VTM and NHW bind multiple EphA receptors [35]) azurin and AzV36-NicL. Abbreviations: Cha-(L)-Cyclohexyl-Alanine, Cam-(L)-SAcetamidomethyl-Cysteine, Nic-Nicotinic acid, Oic-(L)-Octahydroindole-2-carboxylic acid, Tle-(L) tert-Leucine, r-(D)-Arginine, k-(D)-Lysine.

DESCRIPTION OF THE SPECIFIC EMBODIMENTS

Figure 2:
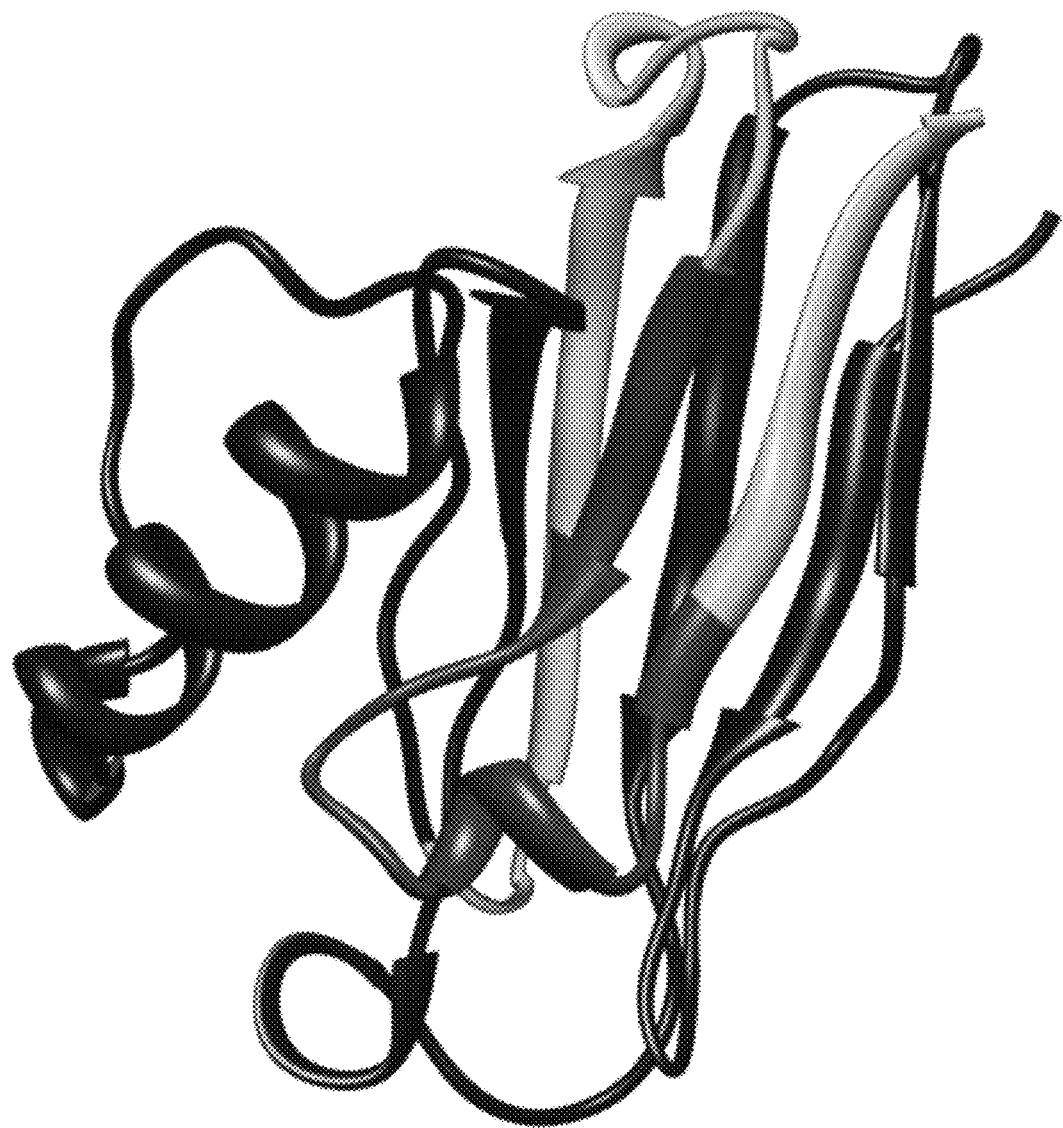
FIG. 2. Structure of Azurin (PDB:1JZG) The sequence of azurin corresponding to AzV36-NicL and those of the other various peptides used in these studies.

Novel compositions and methods are provided for the use of azuvirins and azuvirin analogs as therapeutic and/or prophylactic agents. The peptides are effective at protecting against viral infection, and binding to ephrin receptors. Azuvirin(s) can be administered alone or in combination with other active agents to a patient suffering from an infection in a dose and for a period of time sufficient to reduce the patient population of viruses. Alternatively, a pharmaceutical composition comprising azuvirin is administered as a protective agent to a normal individual facing potential exposure to HIV viruses. Alternatively an azuvirin conjugated to a sensitizer is useful as an anti-cancer drug in combination with radiation therapy.

Specific treatments of interest include, without limitation: using an azuvirin or an azuvirin analog to prevent or treat infection, for example by an enveloped virus, including enveloped retroviruses, more specifically by HIV-1, HIV-2 and related retroviruses that cause Acquired Immunodeficiency Syndrome (AIDS). The azuvirins may be administered alone or in conjunction with other antiviral therapy.

Other specific treatments include the delivering an azuvirin to selectively deliver a chemotherapeutic agent or sensitizer to a cancer cell expressing ephrin receptors, e.g. EphA2 and EphB4.

The peptide form of azuvirins provides a basis for further therapeutic development, by modification of the polypeptide structure to yield modified forms having altered biological and chemical properties. The native or modified forms are formulated in a physiologically acceptable carrier for therapeutic uses, or are otherwise used as an antimicrobial agent.

Azuvirin Compositions

For use in the subject methods, an azuvirin peptide or peptide analog may be used. Azuvirin peptides are generally of from about 10 to 20 amino acids in length, usually from about 12 to 18 amino acids in length, and may be about 13, about 14, about 15, about 16, about 17 residues in length. By the term "amino acid", various analogs of naturally occurring amino acids are intended, including d-amino acids and analogs that include, without limitation, Cha-(L)-cyclohexyl-Alanine, Ctb-(L)-S-t-butyl-Cysteine, Cts-(L)-S-t-butylthio-Cysteine, Cam-(L)-Sacetamidomethyl-Cysteine, Oic-(L)-Octahydroindole-2-carboxylic acid, Tle-(L) tert-Leucine, (D)-Arginine, k-(D)-Lysine, PEG3-11-Amino-3,6,9-trioxaundecanoic acid.

Azuvirins include the peptides set forth in Table 1, although the sequence of the azuvirin polypeptides may be altered in various ways known in the art to generate targeted changes in sequence. The polypeptide will usually be substantially similar to the sequences provided herein, i.e. will differ by one amino acid, and may differ by two amino acids. The sequence changes may be substitutions, insertions or deletions.

| Peptide | Sequence | |
|---|---|---|
| AzV1 | GSGEKDSVTFDVSKLKEGEQYM-Phe-Phe-Cys-Thr-Phe-Pro-GHSA-Leu-Met-KGTLTLK | (SEQ ID NO: 1) |
| AzV2 | GSGEKDSVTFDVSKLKEGEQYM-Phe-Phe-Cys-Thr | (SEQ ID NO: 2) |
| AzV3 | EKDSVTFDVSKLKEGEQYM-Phe-Phe-Cys-Thr-Phe | (SEQ ID NO: 3) |
| AzV4 | VTFDVSKLKEGEQYM-Phe-Phe | (SEQ ID NO: 4) |
| AzV5 | VTFDVSKLKEpEQYM-Phe-Phe | (SEQ ID NO: 5) |
| AzV6 | FDVSKLKEGEQYM-Phe-Phe-Cys-Thr-Phe-Pro-GHSA-Leu-Met-K | (SEQ ID NO: 6) |
| AzV7 | FDVSKLKEGEQYM-Phe-Phe-Cys-Thr-Phe-Pro-GHSA-Leu-Cys-K | (SEQ ID NO: 7) |
| AzV8 | FDVSKLKEGEQYG-Gly-Gly-Cys-Thr-Phe-Pro-GHSA-Leu-Met-K | (SEQ ID NO: 8) |
| AzV9 | FDVSKLKEpEQYM-Gly-Gly-Cys-Thr-Phe-Pro-GHSA-Leu-Cys-K | (SEQ ID NO: 9) |
| AzV10 | FDVSKLKEGEQY | (SEQ ID NO: 10) |
| AzV11 | FDVSKLKEpEQY | (SEQ ID NO: 11) |
| AzV12 | Cys-Thr-Phe-Pro-GHSA-Leu-Met-K | (SEQ ID NO: 12) |
| AzV13 | Cys-Thr-Phe-Pro-GHSA-Leu-Cys-K | (SEQ ID NO: 13) |
| AzV14 | KLKEGEQYM-Phe-Phe-Cys-Thr-Phe-Pro-GH | (SEQ ID NO: 14) |
| AzV15 | KLKEpEQYM-Phe-Phe-Cys-Thr-Phe-Pro-GH | (SEQ ID NO: 15) |
| AzV16 | KLKEGEQYM-Phe-Phe-Cys-Thr-Phe-Pro-GHSA-Leu | (SEQ ID NO: 16) |
| AzV17 | KLKEGEQYM-Phe-Phe-Cys-Thr-Phe-Pro-GHSA-Leu-Met-K | (SEQ ID NO: 17) |
| AzV18 | KLKEGEQYM-Phe-Phe-Cys-Thr-Phe-Pro-GHSA-Leu-Met-KGTLTLK | (SEQ ID NO: 18) |
| AzV19 | EGEQYM-Phe-Phe-Cys-Thr-Phe-Pro-GH | (SEQ ID NO: 19) |
| AzV20 | EGEQYM-Phe-Phe-Cys-Thr-Phe-Pro-GHSA-Leu | (SEQ ID NO: 20) |
| AzV21 | EGEQYM-Phe-Phe-Cys-Thr-Phe-Pro-GHSA-Leu-Met-K | (SEQ ID NO: 21) |
| AzV22 | EGEQYM-Phe-Phe-Cys-Thr-Phe-Pro-GHSA-Leu-Met-KGTLTLK | (SEQ ID NO: 22) |
| AzV23 | YM-Phe-Phe-Cys-Thr-Phe-Pro-GH | (SEQ ID NO: 23) |
| AzV25 | YM-Phe-Phe-Cys-Thr-Phe-Pro-GHSA-Leu | (SEQ ID NO: 24) |
| AzV26 | YM-Phe-Phe-Cys-Thr-Phe-Pro-GHSA-Leu-Met-K | (SEQ ID NO: 25) |
| AzV27 | YM-Phe-Phe-Cys-Thr-Phe-Pro-GHSA-Leu-Met-KGTLTLK | (SEQ ID NO: 26) |
| AzV28 | YM-Phe-Phe-Ser-Thr-Phe-Pro-GHSA-Leu-Met-K | (SEQ ID NO: 27) |
| AzV29 | YM-Phe-Phe-Ctb-Thr-Phe-Pro-GHSA-Leu-Met-K | (SEQ ID NO: 28) |
| AzV30 | YM-Phe-Phe-Cts-Thr-Phe-Pro-GHSA-Leu-Met-K | (SEQ ID NO: 29) |
| AzV31 | YM-Phe-Phe-Cys-Thr-Phe-Pro-GHSA-Leu-Cys-K | (SEQ ID NO: 30) |
| AzV31 | YK-Cha-Cha-Cys-Tle-Cha-Oic-GHRT-Cha-Cys-K | (SEQ ID NO: 31) |
| AzV32 | YK-Cha-Cha-Cys-Tle-Cha-Oic-rHRT-Cha-Cys-k | (SEQ ID NO: 32) |
| AzV33 | YK-Cha-Cha-Cys--r--Cha-Oic-GHRT-Cha-Cys-k | (SEQ ID NO: 33) |
| AzV34 | Yk-Cha-Cha-Cys-Tle-Cha-Oic-GHRT-Cha-Cys-k | (SEQ ID NO: 34) |
| AzV35 | YK-Cha-Cha-Cys--r--Cha-Oic-rHRT-Cha-Cys-k | (SEQ ID NO: 35) |
| AzV36 | Yk-Cha-Cha-Cys-Tle-Cha-Oic-rHRT-Cha-Cys-k | (SEQ ID NO: 36) |
| AzV37 | Yk-Cha-Cha-Cys--r--Cha-Oic-GHRT-Cha-Cys-k | (SEQ ID NO: 37) |
| AzV38 | Yk-Cha-Cha-Cys--r--Cha-Oic-rHRT-Cha-Cys-k | (SEQ ID NO: 38) |
| AzV36-Nic | Yk$^{Nic}$-Cha-Cha-Cys-Tle-Cha-Oic-rHRT-Cha-Cys-k | (SEQ ID NO: 39) |
| AzV36-NicL | Yk$^{Nic}$-Cha-Cha-Cam-Tle-Cha-Oic-rHRT-Cha-Cam-k | (SEQ ID NO: 40) |
| AzV36-L | Yk-Cha-Cha-Cam-Tle-Cha-Oic-rHRT-Cha-Cam-k | (SEQ ID NO: 41) |
| AzV-NicL-Clb | Clb-Yk$^{Nic}$-Cha-Cha-Cam-Tle-Cha-Oic-rHRT-Cha-Cam-k | (SEQ ID NO: 42) |
| AzV-NicL-Mtx | Mtx-PEG$_3$-Yk$^{Nic}$-Cha-Cha-Cam-Tle-Cha-Oic-rHRT-Cha-Cam-k | (SEQ ID NO: 43) |

Peptides of particular interest for cancer applications may include, without limitation, a peptide having a sequence set forth in Table 1, or a variant there, including a conjugate of the peptide and a sensitizer or chemotherapeutic agent. Peptides of particular interest for these purposes bind to one or more ephrin receptors, e.g. as shown in the Examples, and include without limitation AzV17, AzV25, AzV26, AzV31 and AzV36.

The protein may be joined to a wide variety of other therapeutic moieties, stabilizing agents such as PEG and the like, oligopeptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the peptide consists essentially of a polypeptide sequence set forth herein. By "consisting essentially of" in the context of a polypeptide described herein, it is meant that the polypeptide is composed of the sequence set forth in Table 1, which sequence may be flanked by one or more amino acid or other residues that do not materially affect the basic characteristic(s) of the polypeptide.

Azuvirin Coding Sequences

Azuvirin coding sequences can be generated by methods known in the art, e.g. by in vitro synthesis, recombinant methods, etc. to provide a coding sequence to corresponds to an azuvirin polypeptide. Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% by mismatches, and can contain as little as even 5-15%, or 2-5%, or 1-2% by mismatches, as well as a single by mismatch.

Methods of Use

Formulations of azuvirins are administered to a host suffering from an ongoing viral infection or who faces exposure to a viral infection, or to a cancer patient for delivery of a therapeutic moiety. Administration may be topical, localized or systemic. Generally the dosage will be sufficient to decrease the viral population by at least about 50%, usually by at least 1 log, and may be by 2 or more logs. The compounds of the present invention are administered at a dosage that reduces the pathogen population while minimizing any side-effects. It is contemplated that the composition will be obtained and used under the guidance of a physician for in vivo use. Azuvirins are particularly useful for preventing infection by certain viruses, particularly enveloped retroviruses, e.g. enveloped retroviruses such as HIV-1, HIV-2, FIV, and the like.

The susceptibility of a particular virus to killing or inhibition by azuvirins may be determined by in vitro testing, as detailed in the experimental section. Typically a culture of is combined with azuvirins at varying concentrations for a period of time sufficient to allow the protein to act, usually ranging from about one hour to one day. Viral pathogens of interest include retroviral pathogens, e.g. HIV-1; HIV-2, HTLV, FIV, SIV, etc.

Various methods for administration may be employed. For the prevention of HIV infection, administration to mucosal surfaces is of particular interest, e.g. vaginal, rectal, etc. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific azuvirin to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration.

Cancer Applications

For cancer treatment, azuvirin peptides may be conjugated to a therapeutic moiety, such as a radiosensitizer, for photodynamic therapy, cytotoxic agents, and the like.

The term "radiosensitizer," as used herein, is defined as a compound administered to a human or other animal in a therapeutically effective amount to increase the sensitivity of cells to electromagnetic radiation and/or to promote the treatment of diseases that are treatable with electromagnetic radiation. The terms "electromagnetic radiation" and "radiation" as used herein include, but are not limited to, radiation having the wavelength of 10-20 to 100 meters. Preferred embodiments of the present invention employ the electromagnetic radiation of gamma-radiation (10-20 to 10-13 m), X-ray radiation (10-12 to 10-9 m), ultraviolet light (10 nm to 400 nm, visible light (400 nm to 700 nm), infrared radiation (700 nm to 1.0 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include, but are not limited to, hematoporphyrin derivatives, PHOTOFRIN, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Many additional cytotoxic agents are conventionally known and used in the art and may be delivered by the peptides of the invention.

The subject methods are applied to the treatment of tumors. Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. Small cell lung carcinoma is exemplary.

Some cancers of interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

The subject compounds are administered in an effective dose to an individual to inhibit tumor growth, to sensitize tumors to radiation or light therapy, and the like. The dose is effective to increase killing of the targeted cells comparable to the killing of the cells in the absence of the sensitizer, preferably without increased killing of non-targeted cells. Increased killing may be about 10%, about 20%, about 30%, about 40%, about 50%, about 75% about 100%, about 2-fold, 3-fold, 5-fold, 7-fold, 10-fold or more.

The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to sensitize to a therapy, applying the therapy, and determining the effect. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of the compounds can be achieved in various ways, including oral, vaginal, buccal, rectal, parenteral, intraperitoneal, intradermal, transdermal, intratracheal, etc., administration. The azuvirins may be systemic after administration or may be localized by the use of an implant or other formulation that acts to retain the active dose at the site of implantation.

The compounds of the present invention can be administered alone, in combination with each other, or they can be used in combination with other known compounds. In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral, vaginal or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing azuvirins is placed in proximity to the site of infection, so that the local concentration of active agent is increased relative to the rest of the body.

The term “unit dosage form”, as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For use in the subject methods, azuvirins may be formulated with other pharmaceutically active agents, particularly other antimicrobial agents. Antiviral agents, e.g. acyclovir, gancyclovir, etc., and other circular mini-defensins (theta defensins) may also be included in azuvirin formulations for anti-viral use.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Radiotherapy of Lung Cancer Targeting Ephrin Receptors

Lung cancer treatment usually utilizes some form of radiotherapy. We sought to improve the efficacy of such treatment by exploiting targeted delivery of a model radiosensitizer (nicotinamide) to malignant tissues. The molecular target(s) we have chosen is ephrin receptors (Eph) which are overexpressed in many types of cancer, including lung cancer.

Molecular targeting was achieved utilizing a small peptide derived from the C-terminal portion of azurin that belongs to copper-containing redox proteins called cupredoxins and is capable of binding to ephrin receptors. We recently screened sub-library of peptides derived from C-terminal region of azurin and found several small compounds capable of binding selected ephrin receptors: EphA2, EphB2 and EphB4. One of such peptide, termed AzV-36, was chosen for our studies and subsequently conjugated with nicotinic acid via amide bond, shown in FIG. 1. The resulting peptide is linear, 15 residues long, contains 3 D- and several unusual amino acids, and may be easily manufactured in large quantities. Because of its composition, it may possess increased resistance to enzymatic cleavage.

The AzV-36-Nic conjugate was tested in vivo for its ability to radiosensitize Lewis lung carcinoma (LCC) in an artificial metastasis model. Briefly, C57BL/6 mice (8 weeks old) were intravenously injected with $5 \times 10^5$ cells of syngeneic LLC. Various treatments were initiated 4 days later, after cancer engraftment. In general, each animal received intraperitoneally a total of 500 µg (~10 mg/kg) of peptide in 4 daily doses 60 mins before local thoracic irradiation (4 Gy). Animals were sacrificed on the $14^{th}$ day of the experiment and lung tumor nodules were counted.

Studies revealed that nicotinamide targeted to ephrin receptor bearing tumor cells (AzV-36-Nic) increased the efficacy of radiotherapy, with tumor colonies being 3-10 fold lower than with radiation alone depending on experimental schedule. In contrast, equimolar amounts of unconjugated peptide (AzV-36) or nicotinamide alone improved radiation efficacy only 1.3 and 1.2 fold, respectively.

In conclusion, targeted delivery of radio- or photosensitizers to ephrin receptors may be suitable approach in the treatment of lung cancer to significantly improve radiotherapeutic efficacy.

Example 2

Lung cancer treatment usually utilizes some form of radiotherapy. We sought to improve the efficacy of such treatment by exploiting targeted delivery of a model radiosensitizer (nicotinamide) to malignant tissues. The molecular target(s) we have chosen is ephrin receptors (Eph) which are overexpressed in many types of cancer, including lung cancer. Molecular targeting was achieved utilizing a small peptide derived from the C terminal portion of azurin that belongs to copper-containing redox proteins called cupredoxins and is capable of binding to ephrin receptors. We recently screened a sublibrary of peptides derived from the C-terminal region of azurin and found several small compounds capable of binding selected ephrin receptors: EphA2, EphB2 and EphB4. One of these peptides, termed AzV36, was chosen for our studies and subsequently conjugated with nicotinic acid via amide bond. The resulting cyclic peptide AzV39-Nic and its linear counterpart AzV36-NicL are 15 residues long, contain three D- and several unusual amino acids, may be easily manufactured in large quantities and due to their composition, most likely possess increased resistance to enzymatic cleavage. Both conjugates were tested in vivo for ability to radiosensitize Lewis lung carcinoma (LCC) in an artificial metastasis model as well as in a model of subcutaneous engraftment of LLC into syngeneic hosts. Our experiments showed increased efficacy of radiotherapy for both compounds and suggest that targeted delivery of radio- or photosensitizers to ephrin receptors may be a suitable approach in the treatment of lung cancer to significantly improve radiotherapeutic outcome.

Azurin, a member of a family of copper-containing, water soluble, low molecular weight redox proteins called cupredoxins is produced by the pathogenic bacterium *Pseudomonas aeruginosa*. This protein itself possesses anticancer and antiviral activity and also inhibits parasitemia caused by *Plasmodium falciparum*. Azurin can preferentially enter into cancer cells and induce apoptotic cell death in such cells as well as cause significant in vivo regression of melanoma and breast cancer in nude mice. Specific fragments of azurin possess distinct biological properties: for example $Azu_{50-77}$ possesses properties of protein transduction domain allowing azurin for preferential entry into cancer cells, $Azu_{88-113}$ can bind with high affinity to DC-SIGN receptor mimicking the functionality of the intercellular adhesion molecule ICAM-3-natural ligand of DC-SIGN and $Azu_{96-113}$ has a structural similarity to a ligand known as ephrinB2 and binds its cognate receptor tyrosine kinase EphB2. Binding to ephrin receptor(s) is especially interesting since various members of this group have been shown to be overexpressed in various cancers. Therefore ligands capable of selective binding to Eph may possess therapeutic value not only as potential antagonists but also as prospective delivery systems selectively targeting malignant tissues/cells.

To test this hypothesis we synthesized a small library of analogues derived from the C terminal region of azurin ($Azu_{88-128}$) consisting of 40 overlapping sequences containing D—as well as nonproteinaceous amino acids to improve water solubility and resistance to enzymatic degradation. The analogs included the following AzV36    Yk-Cha-Cha-Cys-Tle-Cha-Oic-rHRT-Cha-Cys-k-CONH, (SEQ ID NO. 44)

AzV36-Nic   Yk$_{Nic}$-Cha-Cha-Cys-Tle-Cha-Oic-rHRT-Cha-Cys-k-CONH, (SEQ ID NO. 45)

AzV36-NicL Yk$_{Nic}$-Cha-Cha-Cam-Tle-Cha-Oic-rHRT-Cha-Cam-k-CONH, (SEQ ID NO. 46)

Materials and Methods

Solid-Phase Peptide Synthesis was done with the FastMoc chemical strategy. Analogs were purified by reverse phase HPLC to >95%, and their mass was confirmed by electrospray or MALDI MS.

Binding to selected ephrin receptors was measured by surface plasmon resonance on a Biacore3000 instrument. Commercially available ephrin receptors: EphA2, EphB2 and EphB4 (R&D Systems) were immobilized on a CM-5 chip by amine coupling and tested peptides were passed over a chip surface as analytes.

Animal experiments. Briefly, C57BL/6 mice (8 weeks old) were intravenously injected with $5 \times 10^5$ cells of syngeneic LLC. Various treatments were initiated 4 days later, after cancer engraftment. In general, each animal received intraperitoneally a total of 500 µg (~10 mg/kg) of peptide in 4 daily doses 60 min before local thoracic irradiation (4 Gy). Animals were sacrificed on the $14^{th}$ day of the experiment and lung tumor nodules were counted.

Subcutaneous Engraftment Model.

C57BL/6 mice (8 weeks old) were subcutaneously injected with $1.0 \times 10^6$ cells of syngeneic LLC (leg). After 10 days palpable tumors of approximately 5 mm diameter appeared and treatment was initiated. In general, each animal received intraperitoneally a total of 500 µg (~10 mg/kg) of peptide in 4 daily doses 60 min before local irradiation (4 Gy). Tumors' size was enumerated every two days and animals sacrificed if necessary according to UCLA Animal Care guidelines.

Chemical synthesis of azurin-derived peptides produced diverse library of analogues. We used surface plasmon resonance (SPR) for its screening to select compounds with affinity to selected ephrin receptors: EphA2, EphB2 and EphB4. These particular Ephs were chosen based on their abundance in various cancers to broaden scope of prospective applications. We determined that Eph-binding domain of azurin is most likely located in the region $Azu_{108-122}$ which partially overlap with the previously reported sequence ($Azu_{96-113}$).

Peptides derived from C-terminal region of azurin bound to selected ephrin receptors, although they do not appear to be selective toward single type of receptor (within tested group). Certain positions in the sequence of active peptides are permissive for D-amino acid substituents which can lead to analogues with high resistance to proteolysis.

AzV36-Nic and AzV36-NicL improve efficacy of radiotherapy in artificial metastasis mouse model and linear analog AzV36-NicL appears to be more effective than circular AzV36-Nic. Equimolar doses of nicotinamide alone or peptide lacking Nic residue (AzV36-L) had no or minimal radiosensitizing effect. AzV36-NicL improves also improves efficacy of radiotherapy applied to solid tumors in subcutaneous engraftment model of LLC.

Targeted delivery of radio- or photosensitizers to ephrin receptors provides a suitable approach in the treatment of lung cancer to significantly improve radiotherapeutic efficacy. AzV36-NIcL also constitute a suitable delivery system for "hybrid" anti-cancer therapeutics such as selective radiosensitizing/alklylating compounds.

Example 3

Enhancement of Lung Cancer Radiotherapy by Targeting Ephrin Receptors in a Murine Artificial Metastasis Model Molecular targeting was achieved utilizing a small peptide derived from the C-terminal portion of azurin, a copper-containing redox protein ("cupredoxin") that is capable of binding to ephrin receptors. We prepared and screened a sub-library of peptides derived from the C-terminal region of azurin and found several small analogues that bound ephrin receptors EphA2, EphB2, and EphB4. One such peptide, termed AzV36, was selected for conjugation with nicotinic acid via an amide bond to form AzV36-NicL. The resulting linear peptide contains 15 residues (including unusual and D-amino acids), is very stable in human serum, and can be easily manufactured.

AzV36-NicL conjugate was tested in vivo for its ability to radiosensitize Lewis lung carcinoma (LCC) in artificial metastasis and solid tumor engraftment models. The compound increased the efficacy of radiotherapy with tumor colonies being ~2-13 fold lower than with radiation alone depending on experimental schedule. In contrast, equimolar amounts of unconjugated peptide (AzV36-L) or nicotinamide alone only marginally improved radiation efficacy.

Materials and Methods

All experiments were approved by the UCLA Animal Care and Use Committee (ARC#1999-173-23) and conformed to local and national guidelines. Venous blood samples (uncoded) were collected in the Department of Medicine at UCLA, by a qualified person under the approved Medical Institutional Review Board 2 (MIRB2) protocol (IRB#92-11-596-41) after obtaining written consent from participants.

Peptide synthesis and characterization. All peptides were synthesized by the solid phase method using CEM Liberty automatic microwave peptide synthesizer (CEM Corporation Inc., Matthews, N.C.), applying 9-fluorenylmethyloxycarbonyl (Fmoc) chemistry [57] and standard, commercially available amino acid derivatives and reagents (EMD Biosciences, San Diego, Calif. and Chem-Impex International, Inc., Wood Dale, Ill.). Rink Amide MBHA resin (EMD Biosciences, San Diego, Calif.) was used as a solid support. Peptides were cleaved from resin using modified reagent K (TFA 94% (v/v); phenol, 2% (w/v); water, 2% (v/v); TIS, 1% (v/v); EDT, 1% (v/v); 2 hours) and precipitated by addition of ice-cold diethyl ether. Reduced peptides were purified by preparative reverse-phase high performance liquid chromatography (RP-HPLC) to >95% homogeneity and their purity evaluated by matrix assisted laser desorption ionization spectrometry (MALDI-MS) as well as analytical RP-HPLC.

Disulfide Bond Formation.

Peptides were dissolved at a final concentration of 0.25 mg/ml in 50% DMSO:$H_2O$ and stirred overnight at room temperature. Subsequently peptides were lyophilized and repurified on a preparative C18 SymmetryShield™ RP-HPLC column to >95% homogeneity. Their purity was evaluated by matrix-assisted laser desorption ionization spectrometry (MALDI-MS) as well as by analytical RP-HPLC.

Analytical HPLC.

Analytical reversed-phase HPLC was performed on a Varian ProStar 210 HPLC system equipped with ProStar 325 Dual Wavelength UV-Vis detector with the wavelengths set at 220 nm and 280 nm (Varian Inc., Palo Alto, Calif.). Mobile phases consisted of solvent A, 0.1% TFA in water, and solvent B, 0.1% TFA in acetonitrile. Analyses of peptides were performed with an analytical reversed-phase C18 Symmetry-Shield™ RP18 column, 4.6±250 mm, 5 μm (Waters Corp., Milford, Mass.) applying linear gradient of solvent B from 0 to 100% over 100 min (flow rate: 1 ml/min).

Binding studies. Binding studies were performed by surface plasmon resonance (SPR) on a BIAcore 3000 system (BiaCore AB, Piscataway, N.J.). BIAcore CM5 sensor chips were utilized in all experiments. Binding studies were performed in HBS-EP running buffer (pH=7.4) containing 10 mM HEPES, 150 mM NaCl, 3 mM EDTA, and 0.005% polysorbate 20. Commercially available ephrin receptors: EphA2, EphB2 and EphB4 (R&D Systems, Inc., Minneapolis, Minn.) were immobilized on a CM5 sensor chip using the amine coupling method. The chip was activated by mixing 400 mM N-ethyl-N-(3-dimethylaminopropyl)-carbodiimide hydrochloride and 100 mM N-hydroxysuccinimide. Residual reactive groups on the chip surface were blocked using 1.0 M ethanolamine/HCl (pH=8.5). The flow cell-1 chip, which served as a control, lacked immobilized protein but was treated with N-ethyl-N-(3-dimethylaminopropyl)-carbodiimide hydrochloride, N hydroxysuccinimide, and ethanolamine/HCl. Binding signals were corrected for nonspecific binding by subtracting the flow cell-1 signal (blank surface). To regenerate chip surfaces, bound ligands were removed with 10 mM HCl. Data were analyzed with BIAevaluation 4.1 software (Biacore, Piscataway, N.J.).

Human red blood cells (hRBCs). Fresh blood (~3 ml) was collected from an anonymous donor into a tube that contained heparin as an anticoagulant. An aliquot of blood (200 μl) was removed and washed 4 with 800 μl of cold PBS at room temperature, each centrifugation was for 3 minutes at ~500× g. A total of 780 μl of supernatant was removed each time. With four washes, this procedure should remove >99.8% of the total serum protein and any heparin anticoagulant. The supernatant was completely removed in the last wash, leaving only the packed red blood cells, which were subsequently diluted 1:20 in PBS to make 5% v/v stock of hRBCs.

Hemolysis assay. The experiments were carried out as previously described. Briefly, 2.5% v/v normal human RBCs were exposed to various concentrations of AzV36-NicL at 37° C. for 30 min. All experiment were carried out in triplicate using 96-well microplate (Costar 3596) and OD at 700 nm was monitored every 30 s. employing the SpectraMAX 250 microplate reader (Molecular Devices, Sunnyvale, Calif.). Controls: PBS, human RBCs, human RBCs+2.5% Triton (100% lysis). The hemolytic effect was calculated as following:

$$\% \text{ Hemolysis} = 100 \times \left(1 - \frac{A_{700-Sample} - A_{700-100\% \, Lysis}}{A_{700-NoLysis} - A_{700-100\% \, Lysis}}\right)$$

Experiments were carried out using MultiTox-Fluor Multiplex Cytotoxicity Assay (Promega Corp., Madison, Wis.) as previously described. This assay simultaneously measures the number of live and dead cells in culture wells based on the activity of two proteases, one a marker of cell viability, and the other a marker of cytotoxicity, which yield products with different excitation and emission spectra. Briefly, for cytotoxicity experiments murine LCC (or RAW 264.7) cells were plated in a 96-well plate at a density of $1\times10^4$ cells/well in a total volume of 50 μl of culture media and treated with various concentrations of tested peptides (50 μl of 0-400 μM peptides in culture media). Cells' viability was assessed 24 h later by MultiTox-Fluor Multiplex Cytotoxicity Assay (incubation time 1 h). For cell viability experiments, LCC cells were plated in a 96-well plate at a density of $5\times10^3$ cells/well in a total volume of 50 μl of culture media and treated with various concentrations of tested peptide (50 μl of 0-200 μM peptide in culture media) for 1 hour prior to 0, 2, 4 Gy irradiation. Cell viability was assessed 72 h later by MultiTox-Fluor Multiplex Cytotoxicity Assay (incubation time 1 h). All experiments were carried out in triplicates.

PARP activity assay. Activity of poly (ADP-ribose) polymerase in the presence of the peptide was determined using commercially available HT Universal Colorimetric PARP Assay Kit (cells'-free assay, Trevigen, Inc., Gaithersburg, Md., Cat# 4677-096-K) according to manufacturer's protocol.

Serum stability. Human blood serum was prepared using BD Vacutainer→Rapid Serum Tubes (RST) (BD Diagnostics, Franklin Lakes, N.J.) according to manufacturer's recommendations. Serum was harvested and either used fresh or stored at −80° C. Stability of the AzV36-NicL in the human serum was determined as previously described. Briefly, 50 μl of an aqueous peptide stock solution (10 mg/ml) was added to 1.95 ml of 25% pooled, non-heat inactivated human serum in PBS and incubated at 37° C. Aliquots of 200 μl were collected at different time intervals: 0, 0.5, 1, 2, 4, and 6, 12, 24 h and mixed with 50 μl of TFA. The resulting mixtures were kept at 5° C. for 10 min and then centrifuged at 300 g for 5 min. 100 μl of the supernatants were analyzed using analytical ProStar 210 HPLC system with a ProStar 325 Dual Wavelength detector set at 220 nm and 280 nm (Varian Inc., Palo Alto, Calif.). The mobile phases were: Solvent A, 0.1% TFA (trifluoroacetic acid) in water; solvent B, 0.1% TFA in acetonitrile. Experiments were performed using Vydac 218TP54 C18 column, 4.6×250 mm, 5 μM (Grace Vydac, Hesperia, Calif.) in a linear 0 to 100% gradient of solvent B applied over 100 min at 1 ml/min.

Clonogenic cell survival assay. Exponentially growing murine LCC cells were treated with AzV36-NicL at 0.1, 1, 10, or 20 μM for 0.5 h, irradiated with 0, 2 or 4 Gy, and plated in 100-mm dishes in triplicate. After 8 days, colonies of >50 cells derived from surviving single clonogenic cells were stained with crystal violet in 70% ethanol and counted.

Animal experiments. C57BL/6 gnotobiotic mice (8 weeks old) were obtained from the UCLA AALAC accredited Department of Radiation Oncology Facility and intravenously injected with $5\times10^5$ cells of syngeneic LLC. Various treatments were initiated 4 days later, after cancer engraftment. In general, each animal received intraperitoneally a total of 500 μg (~25 mg/kg) of peptide (or equimolar amount of nicotinamide) in 4 daily doses 60 min before local thoracic irradiation (0 or 4 Gy, total dose: 4.4=16 Gy) that was delivered using an Atomic Energy of Canada cesium gamma irradiator with a dose rate of approximately 0.6 Gy/min with the rest of the body shielded. Prior to irradiation animals were anesthetized by intraperitoneal injection of ketamine/xylazine mixture. Animals were sacrificed on the $14^{th}$ day of the experiment and lung tumor nodules were counted. All experiments were approved by the UCLA Animal Care and Use Committee and conformed to local and national guidelines.

Subcutaneous Engraftment Model.

C57BL/6 mice (8 weeks old) were injected subcutaneously with $1.0\times10^6$ cells of syngeneic LLC (leg). After 10 days, palpable tumors of approximately 5 mm diameter appeared and treatment was initiated. In general, each animal received intraperitoneally a total of 500 μg (~25 mg/kg) of peptide (or equimolar amount of nicotinamide) in 4 daily doses given 60 min before local tumor irradiation (0 or 4 Gy). Tumor size was assessed every two days and animals sacrificed as necessary according to the UCLA Animal Care guidelines.

Results

Figure 3:
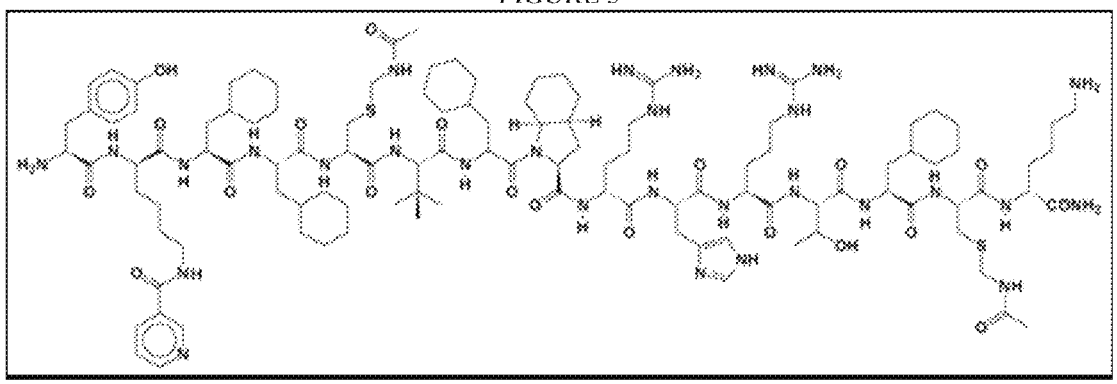
FIG. 3. Chemical structure of AzV36-NicL.

Design and synthesis of Azuvirins (AzVs). FIG. 1 shows sequences of AzV peptides that were synthesized for these studies. The peptides were originally termed "Azuvirins" due to their antiviral properties. As a starting point for creating our mini-library, we used the C-terminal sequence of azurin ($Azu_{88-128}$) which contains protein fragments responsible for: (1) binding to ephrin receptors(s) ($Azu_{96-113}$), and (2) binding to the DC-SIGN receptor ($Azu_{88-113}$). After examining the crystal structure of azurin, we initially synthesized 30 analogues with partially overlapping sequences (AzV1-30). In addition, we synthesized one structurally constrained (disulfide bond clipped) and highly modified analogue AzV31, whose design was intended to preserve or enhance structural features present in the native azurin (please see FIG. 2). Specifically, we introduced modifications that enhanced hydrophobicity in certain positions of the sequence and introduced 2 additional charged residues: Lys and Arg (for details please see FIG. 1). To allow intramolecular disulfide bond formation we also mutated $Met_{121}\rightarrow Cys$, assuming that the resulting structure would resemble part of azurin's copper binding domain and preserve structural feature(s) of this region. Based on initial surface plasmon resonance binding studies (SPR) to selected ephrin receptors we decided that AzV31 had the greatest potential for further development, based on its size, composition and binding properties. Consequently, we used it in a second round of modifications that generally was aimed to generate compounds with enhanced solubility, and improved stability in physiological fluids due to introduction of D-amino acid(s), specifically D-Arg and D-Lys. Placement of these modification(s) took into consideration the structural analysis of $Azu_{107-123}$ region as well as previous experiences. After the resulting compounds, AzV32-38, had undergone a second round of SPR screening, the most promising compound, AzV36 was synthesized and conjugated with a radiosensitizer (nicotinamide) in both a cyclic and a linear format. In the linear version (AzV36-NicL, FIG. 3), cysteine residues present in the original molecule were blocked with acetamidomethyl (Acm) protecting groups. In addition, we also synthesized derivatives of AzV36-NicL N-terminally conjugated with either: (1) the anticancer alkylating agent, chlorambucil (AzV36-NicL-Clb); or (2) the antimetabolite methotrexate (AzV36-NicLMtx) to determine if these modalities could provide additional radiosensitizing or other anticancer effects in our in vivo model.

Figure 4A:
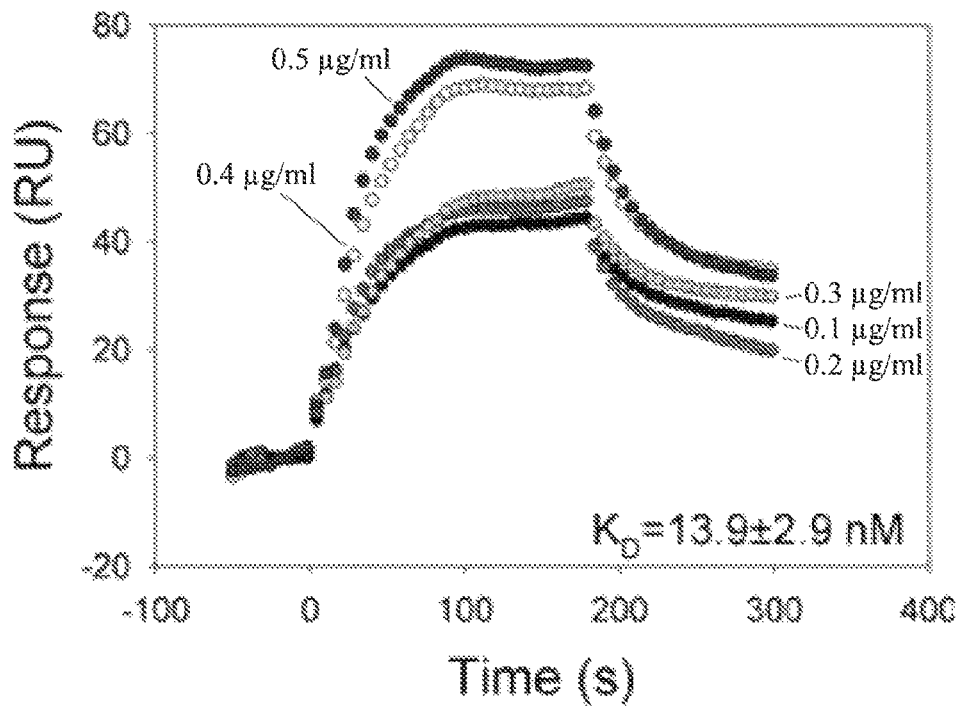
FIG. 4. Surface plasmon resonance binding experiments of AzV36-NicL to rhEphA2 (A), rhEphB2/Fc (B), and rhEphB4 (C)
Figure 4B:
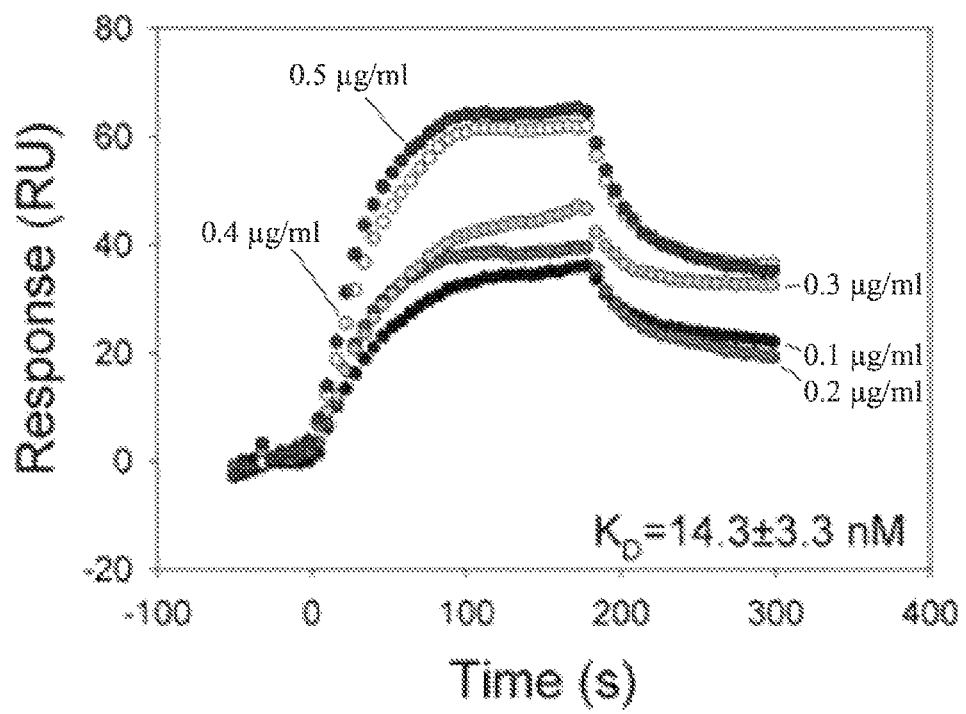
Figure 4C:
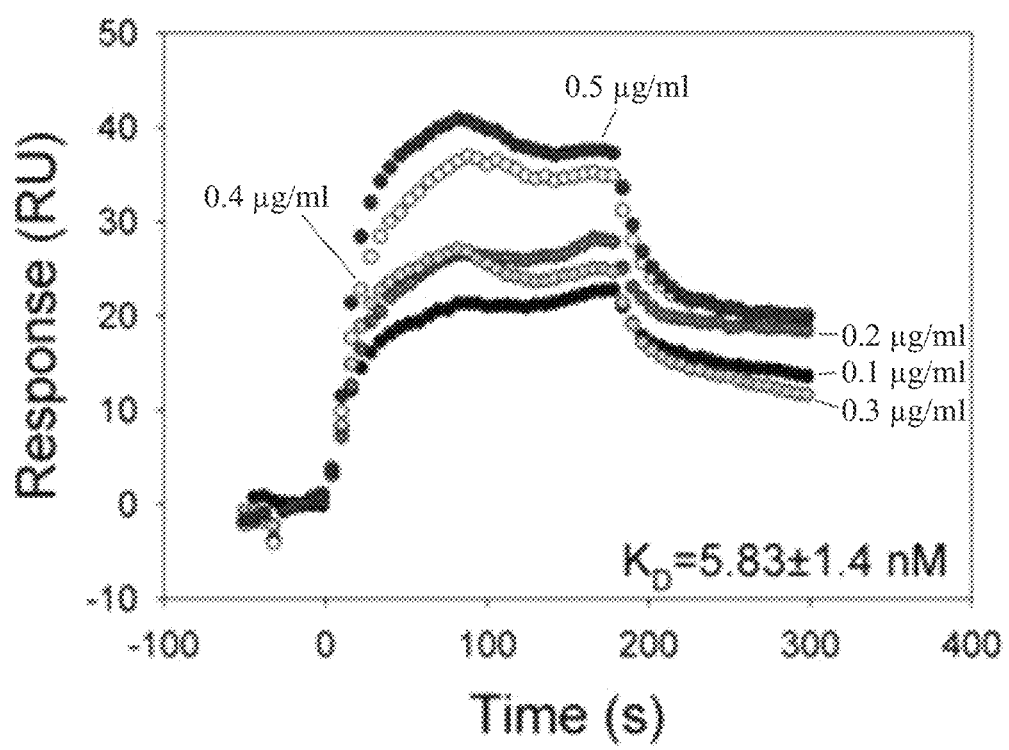

Selected AzVs binds to ephrin receptors EphA2, EphB2 and EphB4. To test whether the synthesized analogs could bind the ephrin receptor(s), we screened the initial group (AzV1-31) using surface plasmon resonance (SPR) spectroscopy. We chose ephrin receptors EphA2, EphB2 and EphB4 as test subjects, based primarily on their abundance in various cancers [20]. From these studies, we determined that the Eph-binding domain of azurin is most likely located in the region $Azu_{108-122}$, which partially overlaps with the previously reported sequence ($Azu_{96-113}$). Binding studies of compounds modified with D- and/or other unusual amino acids (AzV32-AzV38) showed that such peptides retained binding affinity toward tested Ephs and suggested that AzV36 was well suited for further modifications because of its nanomolar $K_D$ values (Table 1) and the presence of 3 D-amino acids that might, in theory, significantly improve its stability in physiological fluids. Its nicotinamide conjugated derivative, AzV36-Nic, as well as its linear counterpart, AzV36-NicL, and linear unconjugated form, AzV36-L, were also tested using SPR. Surprisingly, the unconstrained linear compound AzV36-NicL showed the best binding properties (FIG. 4) with $K_D$ values in low nanomolar range. This peptide was subsequently tested in our in vivo experiments.

Figure 5:
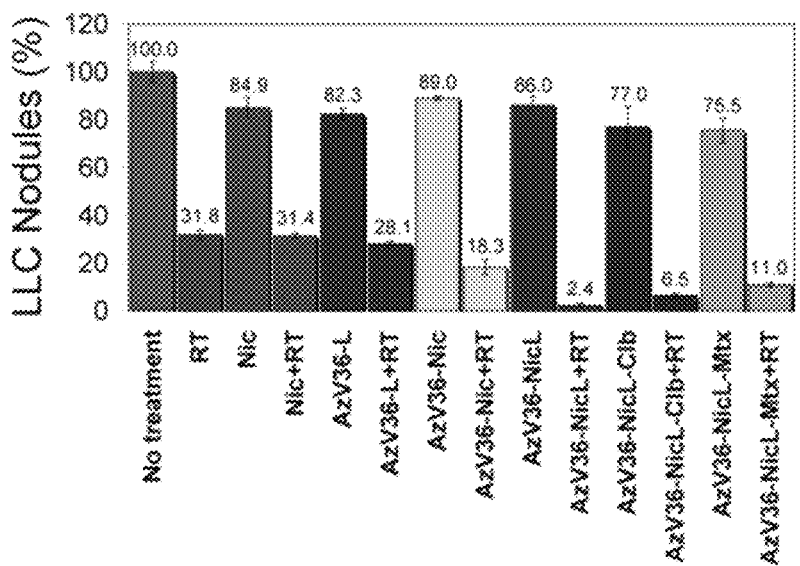
FIG. 5. AzV36-NicL injected starting 4 days after i.v. LLC cells along with RT significantly (P<0.001, ANOVA) decreases tumor colonies that form in the lung, whereas Nic or AzV36-L alone are ineffective. Chlorambucil and methotrexate constructs were less effective than AzV36-NicL. RT-denotes radiation therapy.
Figure 6:
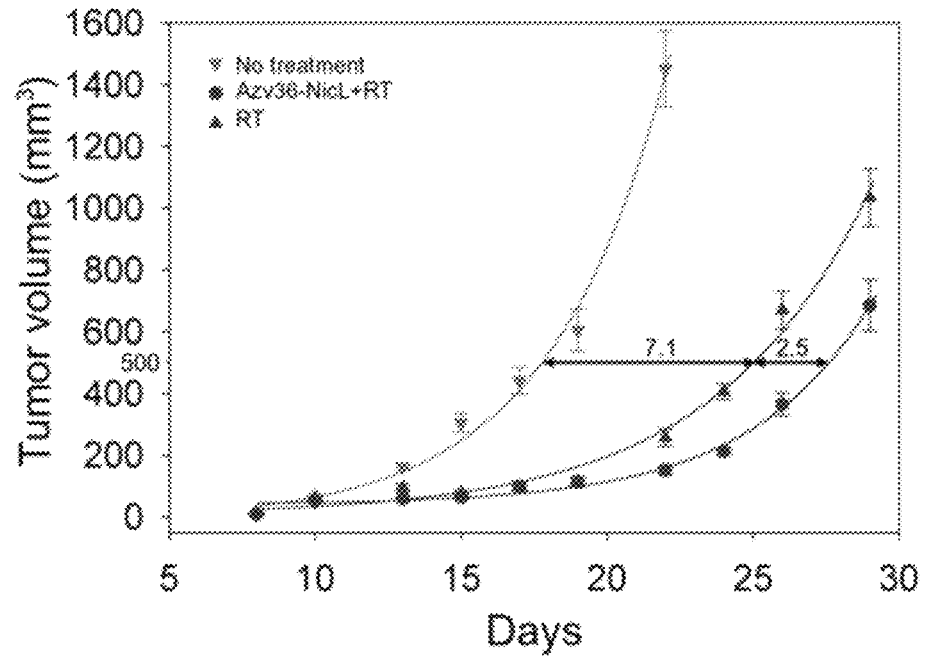
FIG. 6. AzV36-NicL enhances the effect of RT on the growth of LLC in a subcutaneous site (P<0.05, ANOVA). Therapy was initiated when the tumors were about 5 mm in diameter and continued for 4 days.

AzV36-NicL is active in animal models. To determine the effectiveness of this peptide-based-radiosensitizer-targeting strategy, we tested several Nic-conjugates in two in vivo mouse models: an artificial metastasis model and solid tumor engraftment model (FIGS. 5 & 6). The most active in vitro analogue, AzV36-NicL, also showed impressive activity in the artificial metastasis mouse model, increasing the efficacy of radiotherapy about 13-fold, relative to radiation alone. This profound effect is clearly evident in photographs. The same peptide also showed activity in a subcutaneous engraftment mouse model. Radiation treatment alone resulted in ~7.1 days delay in tumor growth and combination of radiation and peptide treatment gave additional ~2.5 days tumor growth delay (FIG. 6). Chlorambucil and methotrexate conjugates (AzV36-NicL-Clb and AzV36-NicL-Mtx respectively) as well as the cyclic derivative AzV36-Nic showed less potency.

Figure 7:
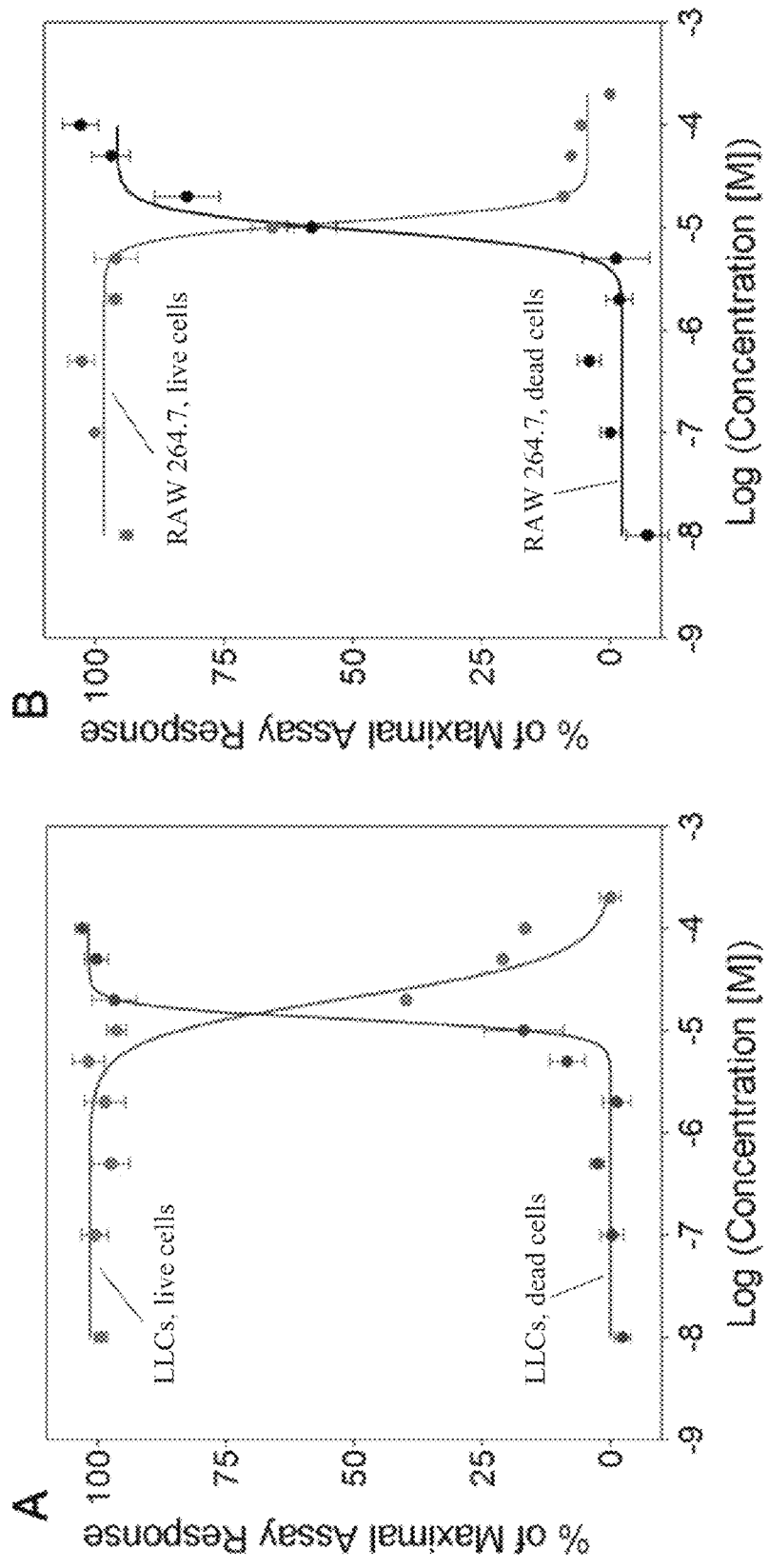
FIG. 7. Toxicity of AzV36-NicL toward Lewis lung carcinoma (panel A) and RAW 264.7 (panel B) cell lines measured after 24 h co-culture with various concentrations of the peptide using MultiTox-Fluor Multiplex Cytotoxicity Assay (Promega Corp., Madison, Wis.). LLCs, live cells, dead cells, RAW 264.7, live cells, (black)-RAW 264.7 dead cells.

Toxicity, hemolysis studies and human serum stability of AzV36-NicL. To ascertain therapeutic potential of our best drug candidate, AzV36-NicL, we performed limited toxicity and stability studies. In vitro toxicity was assessed using the MultiTox-Fluor Multiplex Cytotoxicity Assay. We found (FIG. 7) $LD_{50}$ values of 10.31±0.78 μM for RAW 267 cells and 16.98±2.84 μM for LLC cells. Notably, during in vivo studies using fairly high peptide doses (25 mg/kg IP) no obvious toxic effect of the injections was observed.

Figure 8:
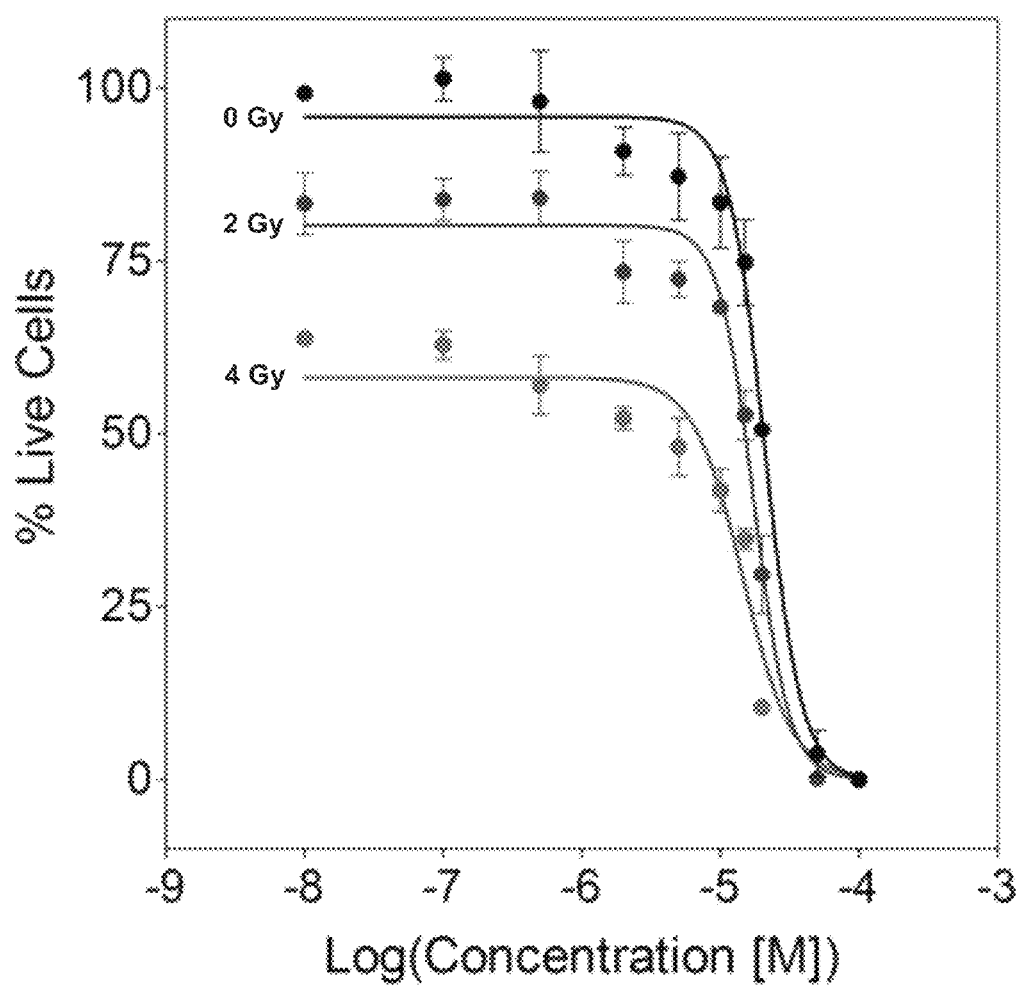
FIG. 8. Radiosensitization of Lewis lung carcinoma cells by effect of AzV36-NicL measured after irradiation at 3 different doses and 72 h co-culture with various concentrations of the peptide using MultiTox-Fluor Multiplex Cytotoxicity Assay (Promega Corp., Madison, Wis.).
Figure 9:
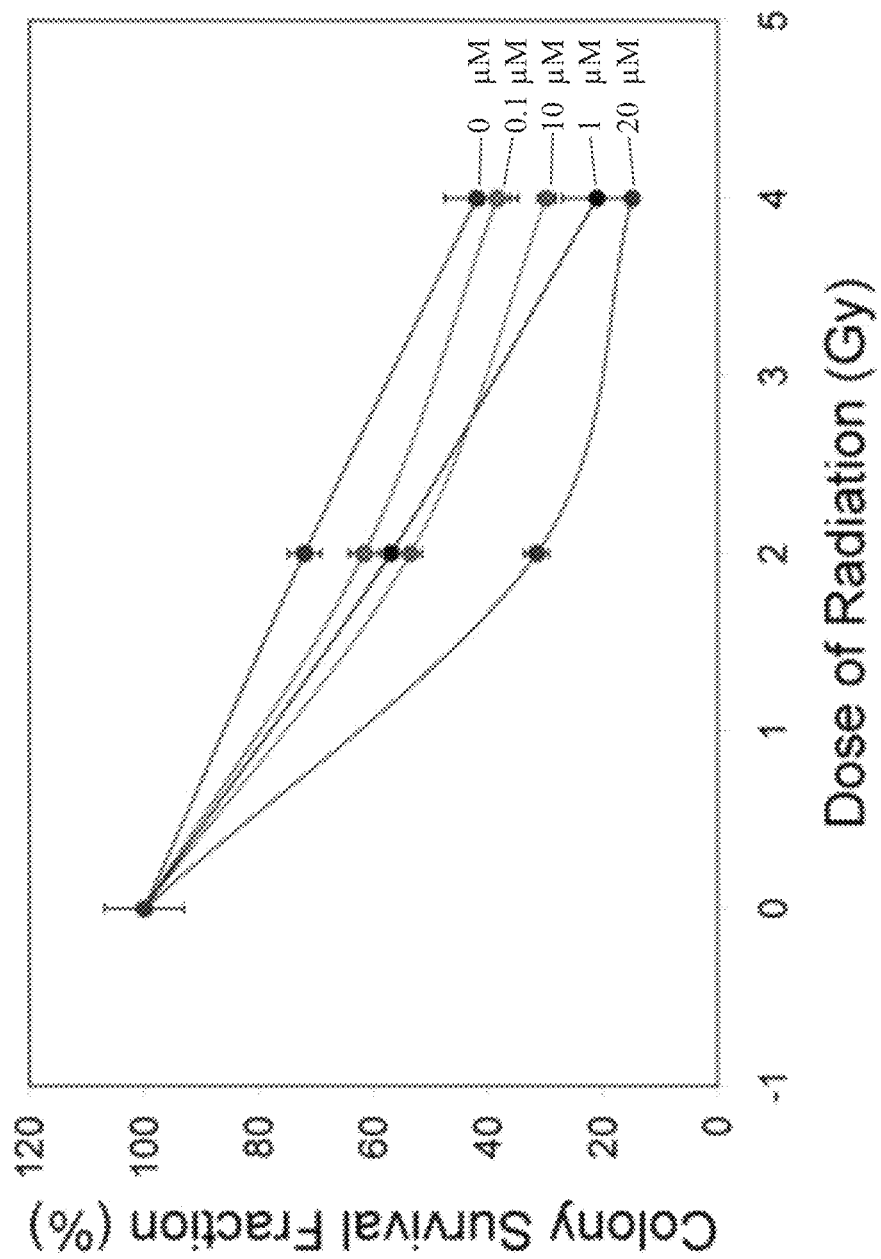
FIG. 9. Clonogenic assay results for LLC cells treated with various concentrations of AzV36-NicL and irradiated at 0, 2 and 4 Gy.
Figure 10:
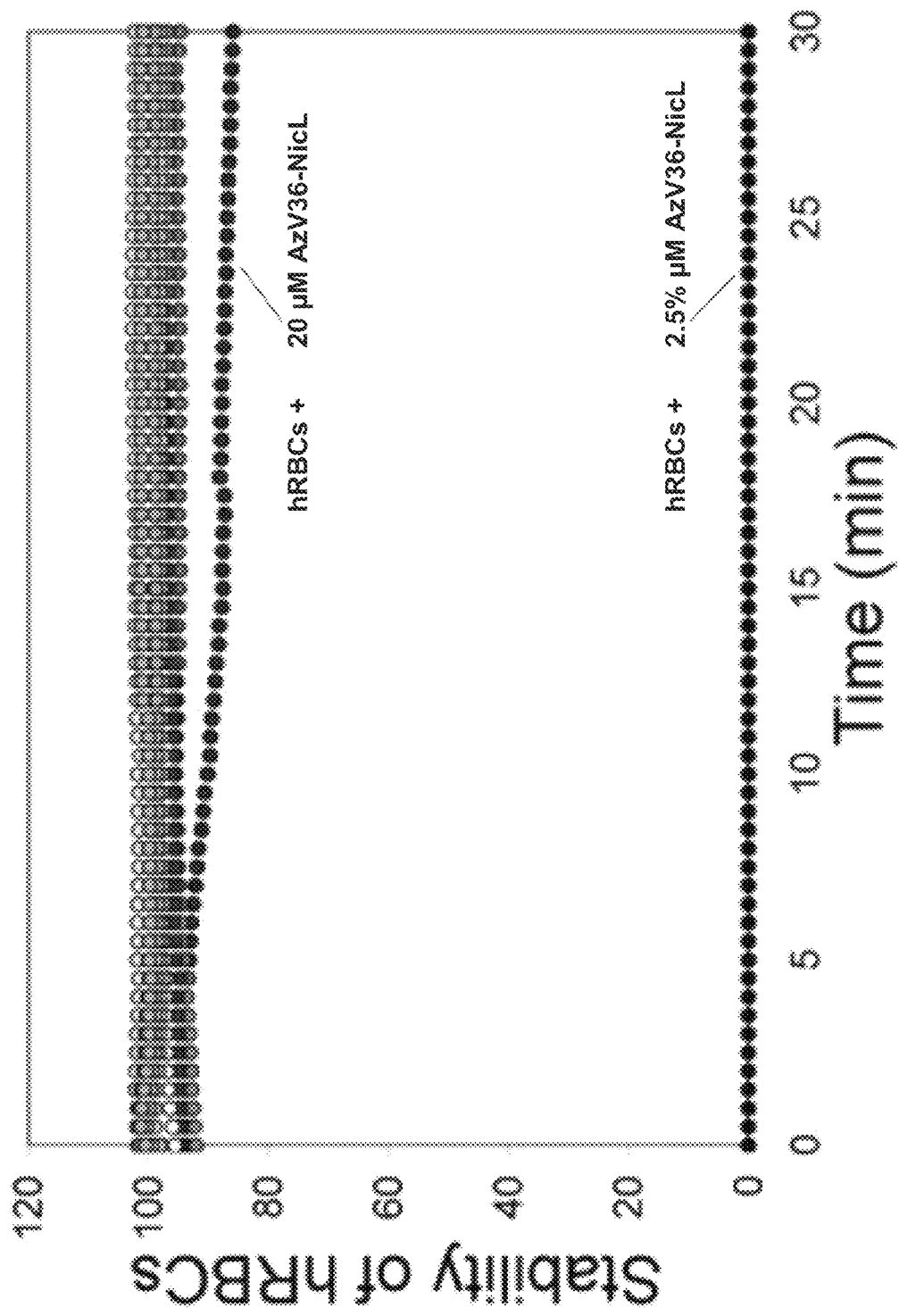
FIG. 10. Stability of hRBCs in the presence of various concentrations of AzV36-NicL. Low hemolytic effect was observed only at 20 µM concentration of the peptide (highest concentration tested, Hemolysis±SEM=9.3±3.0%)
Figure 11:
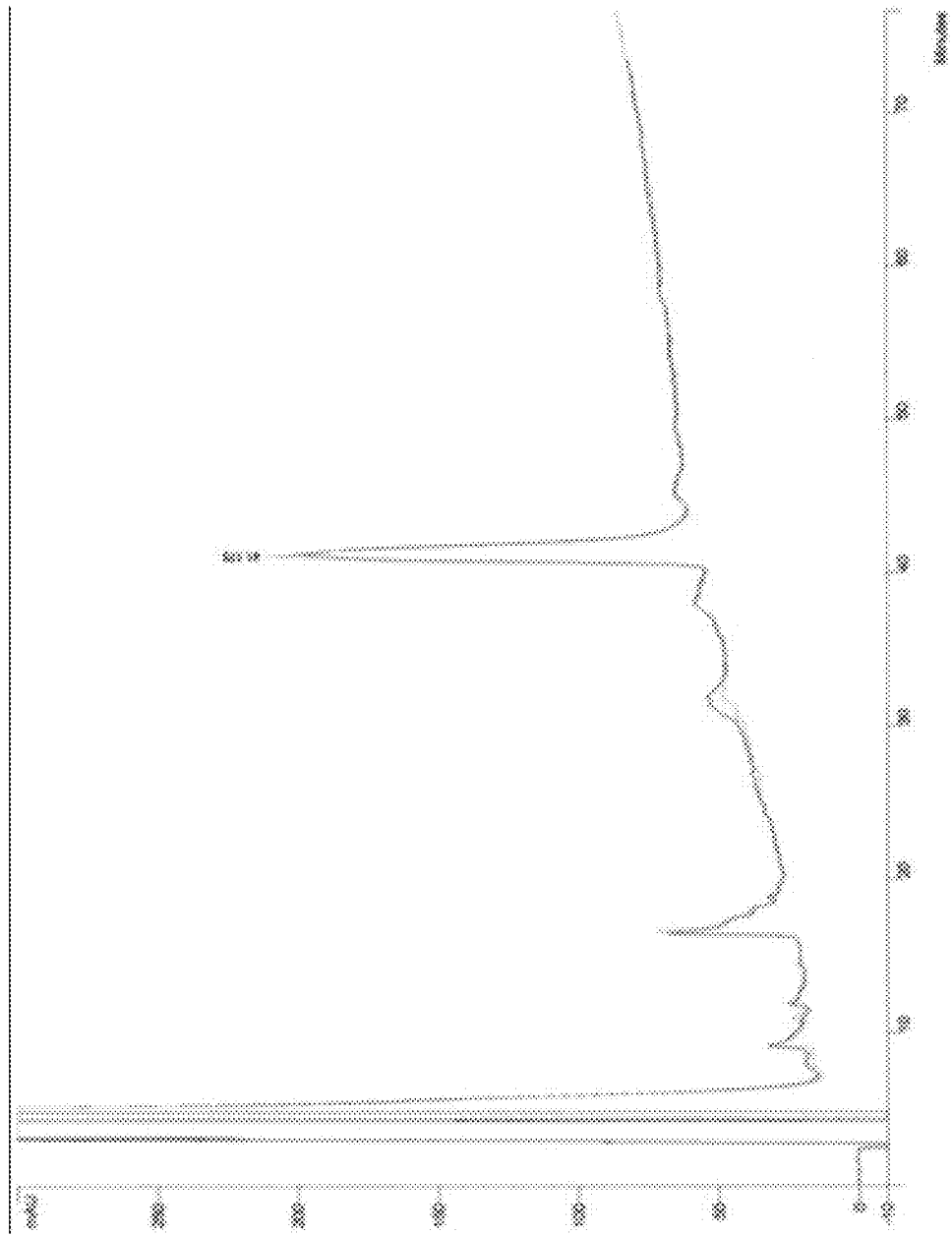
FIG. 11. Stability of AzV36-NicL in the presence of human blood serum. Overlay of representative analytical RP-HPLC profiles at time points T=0 (black) and T=24 h shows remarkable stability of the tested peptide. Based on 8 independent experiments we determined that concentration of the peptide, determined based on AUC (area under the curve), remains unchanged for the period of 24 h (Concentration± SEM=100±0.64%; after 6 days Concentration±SEM= 97.8±2.86%)

Radiosensitizing effect of AzV36-NicL was assessed using a cell viability assay (FIG. 8) and a clonogenic cell survival assay (FIG. 9) showing cytotoxic effects that were peptide-dose-dependent as well as radiation-dose-dependent. The hemolytic effect of the AzV36-NicL toward human red blood cells was measured using a standard hemolytic kinetic assay (FIG. 10). AzV36-NicL showed limited hemolytic properties (Hemolysis=9.3±3.0%) only at the highest tested concentration, 20 μM and was non-hemolytic at ≤10 μM. Stability of the peptide in the human blood serum was determined using RPHPLC based assay (FIG. 11). AzV36-NicL showed remarkable stability over the period of six days with values of 100±0.64% at 24 h time point and 97.8±2.86% after 6 days of incubation at 37° C. Peptide concentrations up to 50 μM did not inhibit poly (ADP-ribose) polymerase (PARP) activity.

TABLE 2

Binding of selected AzV-peptides to rhEphA2, rhEphB2/Fc, and rhEphB4. Presented KD values are averaged from at least 4 independent experiments.

| Peptide | $K_D$ ± SEM (nM) | | |
|---|---|---|---|
| | rhEphA2 | rhEphB2/Fc | rhEphB4 |
| AzV31 | 196 ± 25 | 192 ± 24 | 146 ± 14 |
| AzV32 | 169 ± 29 | 471 ± 160 | 197 ± 90 |
| AzV33 | 100 ± 21 | 106 ± 12 | 78.6 ± 4.5 |
| AzV34 | 196 ± 21 | 189 ± 21 | 135 ± 21 |
| AzV35 | 126 ± 22 | 147 ± 19 | 73.5 ± 3.7 |
| AzV36 | 126 ± 11 | 164 ± 11 | 106 ± 15 |
| AzV37 | 152 ± 38 | 143 ± 37 | 76.0 ± 14 |
| AzV38 | 109 ± 3.5 | 101 ± 2.7 | 46.3 ± 3.8 |
| AzV36-Nic | 425 ± 226 | 251 ± 120 | 138 ± 41 |
| AzV36-NicL | 13.9 ± 2.9 | 14.3 ± 3.3 | 5.83 ± 1.4 |
| AzV36-L | 173 ± 9.9 | 177 ± 4.7 | 166 ± 11 |

External beam radiation therapy is limited by the dose that neighboring healthy tissues can tolerate, even if delivered by conformal approaches. Unfortunately, many require a significantly higher dose of radiation than can be tolerated to achieve a therapeutic cure. For example, renal cell cancer, glioblastoma, and melanoma are generally considered to be radioresistant. In such cases radiosensitizers may prove advantageous provided their effects are limited to the cancer. Interestingly, a number of chemotherapy drugs already approved for cancer treatment act also as radiosensitizers. These include topotecan hydrochloride, paclitaxel, cisplatin, oxaliplatin, 5-fluorouracil, clofarabine, fludarabine, gemcitabine and others, and use of these compounds in treatment regimens in combination with radiotherapy seems to be beneficial, at least in some cases. Most of these target proliferating cells rather than cancer per se, but modern radiation delivery methods that avoid inclusion of large amounts of normal tissue in the field help to increase their therapeutic benefit.

We theorized that additional improvement in therapeutic outcome of radiotherapy and/or chemo-radiotherapy can be achieved by targeted delivery of therapeutic entities to the cancer. Ideally, such therapeutics would be multifaceted compounds containing: (1) a targeting domain, preferably binding with a reasonable affinity to cancer specific molecules (2) a radiosensitizing moiety, for example nicotinamide (Nic) and possibly (3) an additional "therapeutic anti-cancer" domain (e.g., an alkylating or antimetabolite moiety). We prepared a pilot group of such compounds based on the sequence of C terminal portion of azurin that was optimized for binding to selected ephrin receptors: EphA2, EphB2 and EphB4. When the most active compound, AzV36-NicL was subsequently tested in vitro and in vivo, it considerably improved the effects of external beam radiation treatment. AzV36-NicL improved therapeutic outcome of such treatment by factor ~13 (artificial metastasis model) comparing to radiation treatment alone. Its lower activity in the solid tumor engraftment model suggests that peptide may be most active during angiogenesis, since LLC cells express limited levels of ephrin/ephrin receptors that increase considerably during angiogenesis.

The lack of benefit, when radiation therapy was combined with the chorambucil and methotrexate-conjugates suggests that radiosensitization resulted from the nicotinamide moiety, rather than from Eph receptor occupancy per se. This inference is supported by the results obtained after giving Nic alone, vs. giving the unconjugated peptide alone vs. giving the Nic-conjugate (FIG. 5). Presumably, the conjugate establishes a high local concentration of Nic on the surface of LLC cells due to its selective binding to Ephs. This enhances the radiation-driven generation of reactive oxygen species (ROS) that damage the targeted cells. The cytotoxic effect was additionally tested in vitro with LLC cells. In both the cell viability assay (FIG. 8) and a classic clonogenic assay (FIG. 9), the observed cytotoxic effect was concentration dependent with respect to the peptide and dose-dependent with respect to radiation.

The binding affinity of AzV36-NicL toward ephrin receptors (EphA2, EphB2, EphB4) was estimated to be in the low nM range ($K_D \approx 5.8$-14.3 nM). However, a peptide of similar size, called TNYL-RAW was previously reported to be capable of binding EphB4 with even higher affinity, suggesting that binding properties of AzV36-NicL can be further improved. Similarly, peptides SWL and YSA bind with high affinity to EphA2. Comparison of corresponding sequences of Ephs' binding peptides, ephrins, azurin and AzV36-NicL (FIG. 12) revealed similarities between the peptide and other ligands (bolded) that most likely can explain its broad binding properties. It is noteworthy that multiple cancers overexpress more than one ephrin receptor and a change in the Eph expression pattern is often associated with progression to a more aggressive form of disease(s). Therefore therapeutics capable of simultaneously targeting multiple targets associated with various stages of disease may possess higher therapeutic potential than very selective ones.

The simple structure of AzV36-NicL peptide makes it a suitable candidate for further modification to produce analogues with clinically favorable pharmacokinetic properties and novel molecular targeting. The peptide already possesses limited toxicity and hemolytic properties, and probably could be further engineered to improve these variables. Noteworthy, AzV36-NicL can be easily manufactured in large quantities and also modified for derivatization using standard protocols, which allows for its conjugation with various compounds via amide bond linkage. In addition, it contains several unusual and D-amino acids that confer increased stability in physiological conditions making AzV36-NicL and its derivatives attractive drug candidates. Since external beam radiation therapy is widely used in cancer treatment, compounds able to significantly increase its efficacy and limit collateral damage to neighboring healthy tissues/cells (due to selective delivery of radiosensitizer to cancer cells) have broad therapeutic potential.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated AzV36 azuvirin peptide comprising an AzV36 azuvirin peptide sequence of SEQ ID NO:36 and conjugated to a radiosensitizer.

2. The peptide of claim 1, wherein the radiosensitizer is nicotinamide.

3. The peptide of claim 1, and a pharmaceutically acceptable excipient.

4. An isolated AzV36 azuvirin peptide comprising an AzV36 azuvirin peptide sequence of SEQ ID NO:39.

5. An isolated AzV36 azuvirin peptide comprising an AzV36 azuvirin peptide sequence of SEQ ID NO:40.

* * * * *